US010207982B2

(12) United States Patent
Domínguez Chávez et al.

(10) Patent No.: US 10,207,982 B2
(45) Date of Patent: Feb. 19, 2019

(54) SOLID FORMS OF DESVENLAFAXINE

(71) Applicant: ALPARIS, S.A. DE C.V., Mexico D.F. (MX)

(72) Inventors: Jorge Guillermo Domínguez Chávez, Cuernavaca (MX); Karina Mondragón Vásquez, Cuernavaca (MX); Hugo Morales Rojas, Cuernavaca (MX); Dea Herrera Ruiz, Cuernavaca (MX); Herbert Höpfl, Cuernavaca (MX); Reyna Reyes Martínez, Cuernavaca (MX); Javier Hernández Illescas, Cuernavaca (MX); Juan Pablo Senosiain Peláez, Mexico D.F. (MX)

(73) Assignee: Alparis, S.A. DE C.V., Mexico D.F. (MX)

( * ) Notice: Subject to any disclaimer, the term of this patent is extended or adjusted under 35 U.S.C. 154(b) by 0 days.

(21) Appl. No.: 15/636,818

(22) Filed: Jun. 29, 2017

(65) Prior Publication Data
US 2018/0002273 A1    Jan. 4, 2018

(30) Foreign Application Priority Data

Jun. 29, 2016   (MX) .................... MX/a/2016/008646

(51) Int. Cl.
| | |
|---|---|
| *C07C 215/64* | (2006.01) |
| *C07C 65/05* | (2006.01) |
| *C07C 65/03* | (2006.01) |
| *C07C 213/10* | (2006.01) |
| *A61K 31/137* | (2006.01) |
| *B01D 9/02* | (2006.01) |
| *B01L 9/02* | (2006.01) |

(52) U.S. Cl.
CPC .......... *C07C 215/64* (2013.01); *A61K 31/137* (2013.01); *B01L 9/02* (2013.01); *C07C 65/03* (2013.01); *C07C 65/05* (2013.01); *C07C 213/10* (2013.01); *C07B 2200/13* (2013.01); *C07C 2601/14* (2017.05)

(58) Field of Classification Search
CPC ....... C07C 215/64; C07C 65/05; C07C 65/03; C07C 213/10; A61K 31/137; B01D 9/02
See application file for complete search history.

(56) References Cited

U.S. PATENT DOCUMENTS

| | | |
|---|---|---|
| 4,535,186 A | 8/1985 | Husbands et al. |
| 8,481,596 B2 | 7/2013 | Singh et al. |
| 2009/0246284 A1 | 10/2009 | Sebastian et al. |
| 2011/0082213 A1 | 4/2011 | Borut et al. |
| 2011/0112200 A1* | 5/2011 | Niddam-Hildesheim ................... C07C 51/313 514/649 |
| 2013/0028937 A1 | 1/2013 | Plata Salaman et al. |

FOREIGN PATENT DOCUMENTS

| | | |
|---|---|---|
| WO | 0032555 A1 | 6/2000 |
| WO | 0059851 A1 | 10/2000 |
| WO | 02064543 A2 | 8/2002 |
| WO | 2009053840 A2 | 4/2009 |
| WO | 2009138234 A1 | 11/2009 |
| WO | 2010060390 A1 | 6/2010 |
| WO | 2011006455 A2 | 1/2011 |

OTHER PUBLICATIONS

Newman et al., 2003, DDT vol. 8 No. 19, 898-905.*
Chawla et al., CRIPS vol. 5 No. 1, Sep. 12, 2004.*
Desvenlafaxine, 2018, https://en.wikipedia.org/wiki/Desvenlafaxine.*
Polymorph, 2018, https://www.ssci-inc.com/publications/what-everyone-needs-to-know-about-polymorphs/.*
Semisolid, 2018, https://simple.wikipedia.org/wiki/Semisolid.*
Amorphous, 2018, https://simple.wikipedia.org/wiki/Amorphous_solid.*
Polymorphism, 2018, https://en.wikipedia.org/wiki/Polymorphism_(materials_science).*
Spinelli et al., Crystal Growth & Design, 2017, 17, 4270-4279.*

* cited by examiner

*Primary Examiner* — Sun Jae Yoo
(74) *Attorney, Agent, or Firm* — Saul Ewing Arnstein & Lehr LLP; Debora Plehn-Dujowich; Domingos J. Silva

(57) ABSTRACT

The present invention refers to new amorphous and crystalline solid forms of desvenlafaxine, also known as O-desmethylvenlafaxine or desmethylvenlafaxine, and to its salts, solvates, hydrates and polymorphs thereof, as well as to their use in the manufacture of a pharmaceutical composition useful in the treatment of depression and/or as a selective serotonin and norepinephrine reuptake inhibitor and also in menopause-associated vasomotor disorders.

5 Claims, 26 Drawing Sheets

SOLID FORMS OF DESVENLAFAXINE

CROSS-REFERENCE TO RELATED APPLICATIONS

The present application claims priority to Mexican Patent Application No. MX/a/2016/008646, filed Jun. 29, 2016, which application is incorporated by reference herein in its entirety.

FIELD OF THE INVENTION

The present invention refers to new solid amorphous and crystalline forms of desvenlafaxine, also known as 0-desmethylvenlafaxine or desmethylvenlafaxine, and to the salts, solvates, hydrates and polymorphs thereof, as well al to their use in the manufacture of a pharmaceutical composition useful in the treatment of depression and/or selective serotonin and norepinephrine reuptake inhibitor and in menopause-associated vasomotor disorders.

BACKGROUND OF THE INVENTION

Desvenlafaxine is the main active metabolite of venlafaxine; it is also known as O-desmethylvenlafaxine or desmethylvenlafaxine; it is a selective serotonin and noradrenaline reuptake inhibitor (SSNRI), represented by the following structural formula:

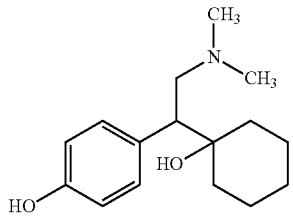 [SMILES: CN(C)CC(c1ccc(O)cc1)C1(O)CCCCC1]

Desvenlafaxine (DSV), chemical name (±)-1-[2-(dimethylamino)-1-(4-hydroxyphenyl)ethyl]cyclohexanol, as well as its pharmaceutically acceptable salts, were firstly described in U.S. Pat. No. 4,535,186, which is incorporated herein in its entirety by reference.

Desvenlafaxine free base can also be named as desvenlafaxine base, or pure or neutral desvenlafaxine. Desvenlafaxine is administered orally, mainly as the succinate salt, for the treatment of depression and menopause-associated vasomotor disorders. Preferably, it is administered as modified-release preparations.

The dose used is from 50 mg to 400 mg per day, preferably once per day. High doses of 400 mg per day can be associated with adverse effects.

Doses between 100 mg and 200 mg per day are not recommended in patients with moderate to severe hepatic insufficiency.

Some patent documents describe the process for preparing desvenlafaxine and its salts, purification methods thereof and pharmaceutical compositions, but none of them refers to the NSF of desvenlafaxine described in the present invention.

Patent document WO2000032555 (U.S. Pat. No. 6,197,828) of Sepracor describes desvenlafaxine base also known as free, neutral or pure base.

Documents WO2002064543 (U.S. Pat. No. 6,673,838) of Wyeth, and WO2000059851 (U.S. Pat. No. 8,269,040) of Sepracor, refer to the product 0-desmethylvenlafaxine succinate.

Documents US2011082213 of Lek Pharma; WO2010060390 and WO2011006455 of Zenti-Va, describe the preparation of desvenlafaxine and/or salts such as D-glucuronate monohydrate, orotic acid, among others.

Documents WO2009138234 of KRKA Tovarna and U.S. Pat. No. 8,481,596 of Lupin Ltd, describe processes for preparing desvenlafaxine using p-toluenesulfonic acid and benzoic acid.

Document WO2009053840 (US2011046231) of Actavis Group PTC, describes desvenlafaxine salts selected from oxalate, benzoate and lactate salts with addition salts of hydrochloric, sulfuric and toluenesulfonic acid, among others.

Document US20090246284 of Actavis Group describes a co-crystal comprising ortho-desmethylvenlafaxine and succinic acid.

Document US20130028937 of Esteve Laboratories refers to a co-crystal of venlafaxine and celecoxib.

No documents referring to the preparation of new solid forms of desvenlafaxine with hydroxybenzoic acid, for example, 3-hydroxybenzoic acid (3-HB), 3,4-dihydroxybenzoic acid (3,4-DHB) and 3,4,5-trihydroxybenzoic acid (3,4,5-THB), among others, were located in the state of the art.

A great amount of combinations with possible co-formers can be envisaged during the process of obtaining new solid forms, however only some of those combinations generate a stable solid form, as demonstrated in the specification of the present application.

BRIEF SUMMARY OF THE INVENTION

The present invention refers to new solid forms (NSF) of desvenlafaxine (DSV), which have a constant quality and which can show enhanced physicochemical properties such as chemical and physical stability, enhanced flow properties and modified dissolution rate.

In the present invention, the term "new solid forms" (NSF) refers to any solid material (phase) which presents intermolecular interactions among at least two independent molecular entities, in any stoichiometric relationship, wherein at least one of the independent molecular entities is a pharmaceutical entity.

These new solid forms contain at least one therapeutic molecule also known as drug, in this case desvenlafaxine, and a pharmaceutically acceptable counter-ion or co-former.

In the present invention, the new solid forms (NSF) of desvenlafaxine (DSV) are obtained by chemically or physically combining the drug with co-formers. The co-formers used in the present invention possess one or more hydroxyl and carboxyl groups, which can form new molecules or complexes through ionic interactions, hydrogen bonding and/or Van der Waals' links with desvenlafaxine or other active agents having similar structural features, such as venlafaxine or another cycloalkane ethylamine.

The Co-Formers Employed in the Present Invention are:
2-hydroxybenzoic acid or 2-HB or o-HB;
3-hydroxybenzoic acid or 3-HB or m-HB;
4-hydroxybenzoic acid or 4-HB or p-HB, also known as salicylic acid;
2,3-dihydroxybenzoic acid or 2,3-DHB or hypogallic acid;
2,4-dihydroxybenzoic acid or 2,4-DHB or β-resorcylic acid;
2,5-dihydroxybenzoic acid or 2,5-DHB or gentisic acid;
2,6-dihydroxybenzoic acid or 2,6-DHB or γ-resorcylic acid;
3,4-dihydroxybenzoic acid or 3,4-DHB or protocatechuic acid;
3,5-dihydroxybenzoic or 3,5-DHB or α-resorcylic acid;
3,4,5-trihydroxybenzoic acid or 3,4,5-THB or gallic acid.

BRIEF DESCRIPTION OF THE DRAWINGS

The following figures illustrate the characterization of the NSF of desvenlafaxine by IR spectroscopy, X-ray powder diffraction (XRPD) and calorimetric analysis DSC-TGA.

FIGS. 4A-4C. Comparison of dissolution rate profiles in: FIG. 4A) phosphate buffer (pH=6.8), FIG. 4B) acetate buffer (pH=4.8) and FIG. 4C) HCl solution pH 1.2, for neutral desvenlafaxine (line with squares (■)), new amorphous solid phase of desvenlafaxine-3,4-dihydroxybenzoic acid (line with circles (●)) and the physical mixture of desvenlafaxine with 3,4-dihydroxybenzoic acid (line with triangles (▲)).

FIGS. 4D-4F. Comparison of dissolution rate profiles in: FIG. 4D) phosphate buffer (pH=6.8), FIG. 4E) acetate buffer (pH=4.8) and FIG. 4F) HCl solution pH 1.2 for neutral desvenlafaxine (line with squares (■)), the new amorphous solid phase of desvenlafaxine-3,4,5-trihydroxybenzoic acid (line with circles (●)) and the physical mixture of desvenlafaxine with 3,4,5-trihydroxybenzoic acid (line with triangles (▲)).

FIGS. 4G-4I. Comparison of dissolution rate profiles in: FIG. 4G) phosphate buffer (pH=6.8), FIG. 4H) acetate buffer (pH=4.8) and FIG. 4I) HCl solution pH 1.2 for the new amorphous solid phase of desvenlafaxine-3-hydroxybenzoic acid (line with circles (●)) and the physical mixture of desvenlafaxine with 3-hydroxybenzoic acid (line with triangles (▲)), FIG. 5A. Powder diffractograms obtained from the stability test for: a) neutral desvenlafaxine, b) 3,4,5-trihydroxybenzoic acid co-former, c) initial new amorphous solid phase of desvenlafaxine-3,4,5-trihydroxybenzoic acid, d) amorphous phase subjected to 45° C. in dry conditions, and e) amorphous phase subjected to 50° C. in dry conditions.

DETAILED DESCRIPTION

Figure 1A:
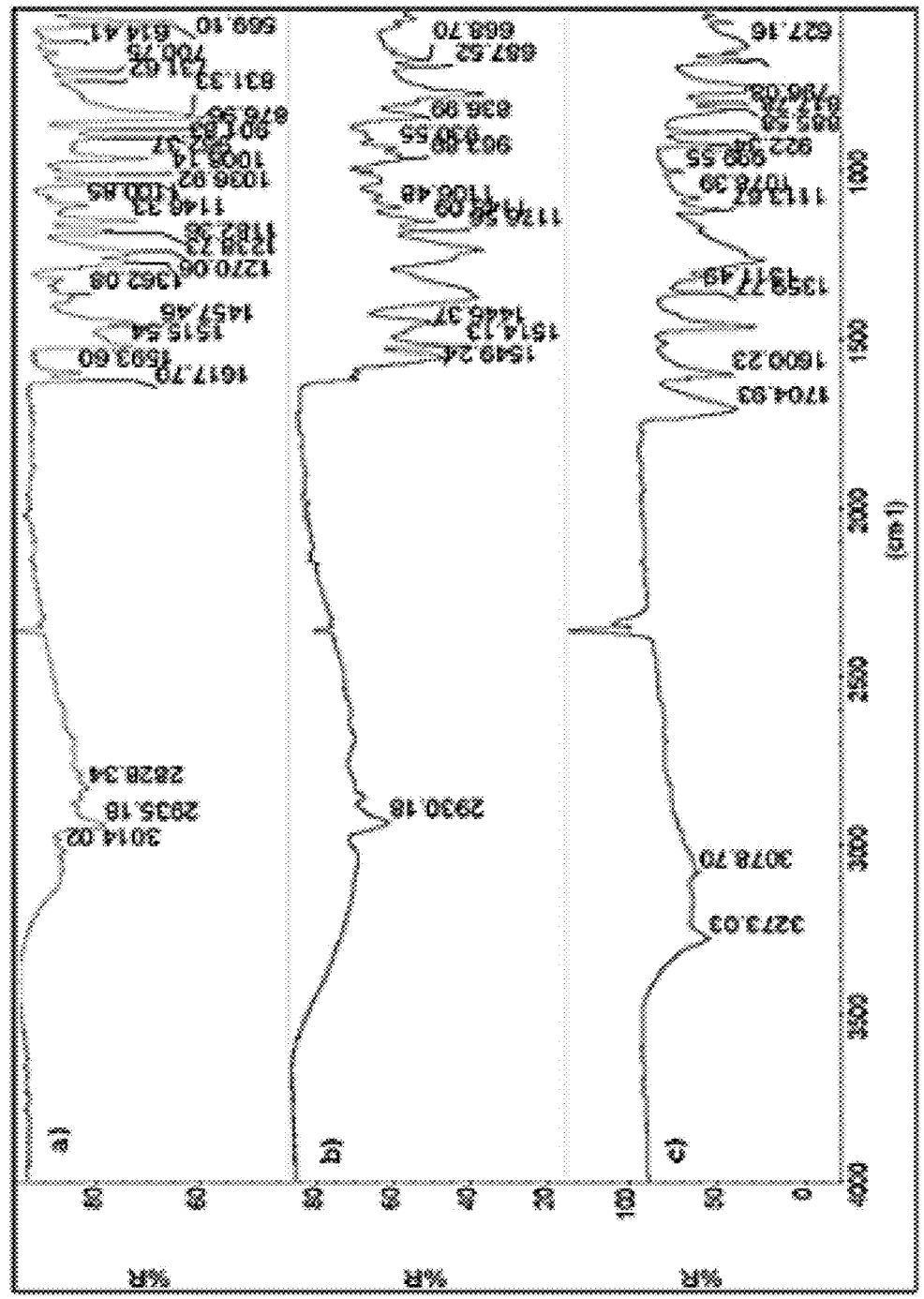
FIG. 1A. IR Spectrum of: a) neutral desvenlafaxine, b) new amorphous solid phase of desvenlafaxine-3-hydroxybenzoic acid, and c) 3-hydroxybenzoic acid.

The present invention describes in detail the preparation of new solid forms of DSV, amorphous and crystalline, starting from neutral DSV and the interaction with the selected co-formers. The proposed hydroxybenzoic acid co-formers show a pKa from 1.2 to 4.5.

New Amorphous Solid Forms

The present invention shows the formation of new stable amorphous solid phases (NSF) such as desvenlafaxine-3,4,5-trihydroxybenzoic acid (DSV:3,4,5-THB), desvenlafaxine-3,4-dihydroxybenzoic acid (DSV:3,4-DHB) and desvenlafaxine-3-hydroxybenzoic acid (DSV:3-HB).

The present invention exhibits the amorphous NSF formed from a selective serotonin and noradrenaline reuptake inhibitor (desvenlafaxine or DSV) and a co-former X: wherein X possesses one or several hydroxyl groups and one carboxyl group, and can form a new chemical entity through ionic interactions or intermolecular forces, such as but not limited to hydrogen bonding and/or van der Waals' links; as well as the solvates, hydrates and/or polymorphs of DSV:X. The co-former X is selected from: 2-hydroxybenzoic acid (2-HB), 3-hydroxybenzoic acid (3-HB), 4-hydroxybenzoic acid (4-HB), 2,3-dihydroxybenzoic acid (2,3-DHB), 2,4-dihydroxybenzoic acid (2,4-DHB), 2,5-dihydroxybenzoic acid (2,5-DHB), 2,6-dihydroxybenzoic acid (2,6-DHB), 3,4-dihydroxybenzoic acid (3,4-DHB), 3,5-dihydroxybenzoic acid (3,5-DHB) and 3,4,5-trihydroxybenzoic acid (3,4,5-THB).

Each new solid phase is characterized by X-Ray Powder Diffraction, Infrared and Raman Spectroscopy, and Thermal Analysis by Differential Scanning calorimetry and Thermogravimetric Analysis.

The following example is not limitative of the process for obtaining the new amorphous solid forms.

a) Dissolving a stochiometric mixture drug-co-former 1:1 in a polar dissolvent selected, for example, from methanol, ethanol, ethanol 96°, acetone and mixtures thereof.

b) The mixture is placed in a rotary evaporator in a 70-80° C. bath for assisted evaporation with a vacuum pump, until complete solvent evaporation.

c) Heating is maintained under reduced pressure to ensure complete solvent evaporation.

d) The resulting solid is extracted from the container and is placed in closed vials for its complete characterization.

Results and Characterization

A visual analysis was performed to the NSF obtained from desvenlafaxine with the several co-formers. In some cases, dry and manageable foamy solids were obtained, and in other cases, semisolids of unctuous aspect and not very manageable were produced, as detailed in Table 1.

TABLE 1

NSF and their appearance after being synthesized

| New solid form | Appearance of the amorphous solid |
|---|---|
| DSV:2-HB | Semisolid |
| DSV:3-HB | Foamy solid |
| DSV:4-HB | Semisolid |
| DSV:2,3-DHB | Foamy solid |
| DSV:2,4-DHB | Semisolid |
| DSV:2,5-DHB | Semisolid |
| DSV:2,6-DHB | Semisolid |
| DSV:3,4-DHB | Foamy solid |
| DSV:3,5-DHB | Semisolid |
| DSV:3,4,5-THB | Foamy solid |

Characterization of Amorphous NSF by Infrared Spectroscopy

Infrared spectroscopy is sensitive to the formation of intermolecular forces such as hydrogen bonding and ion-pair formation, and it is an important tool in the determination of NSF.

Figure 1B:
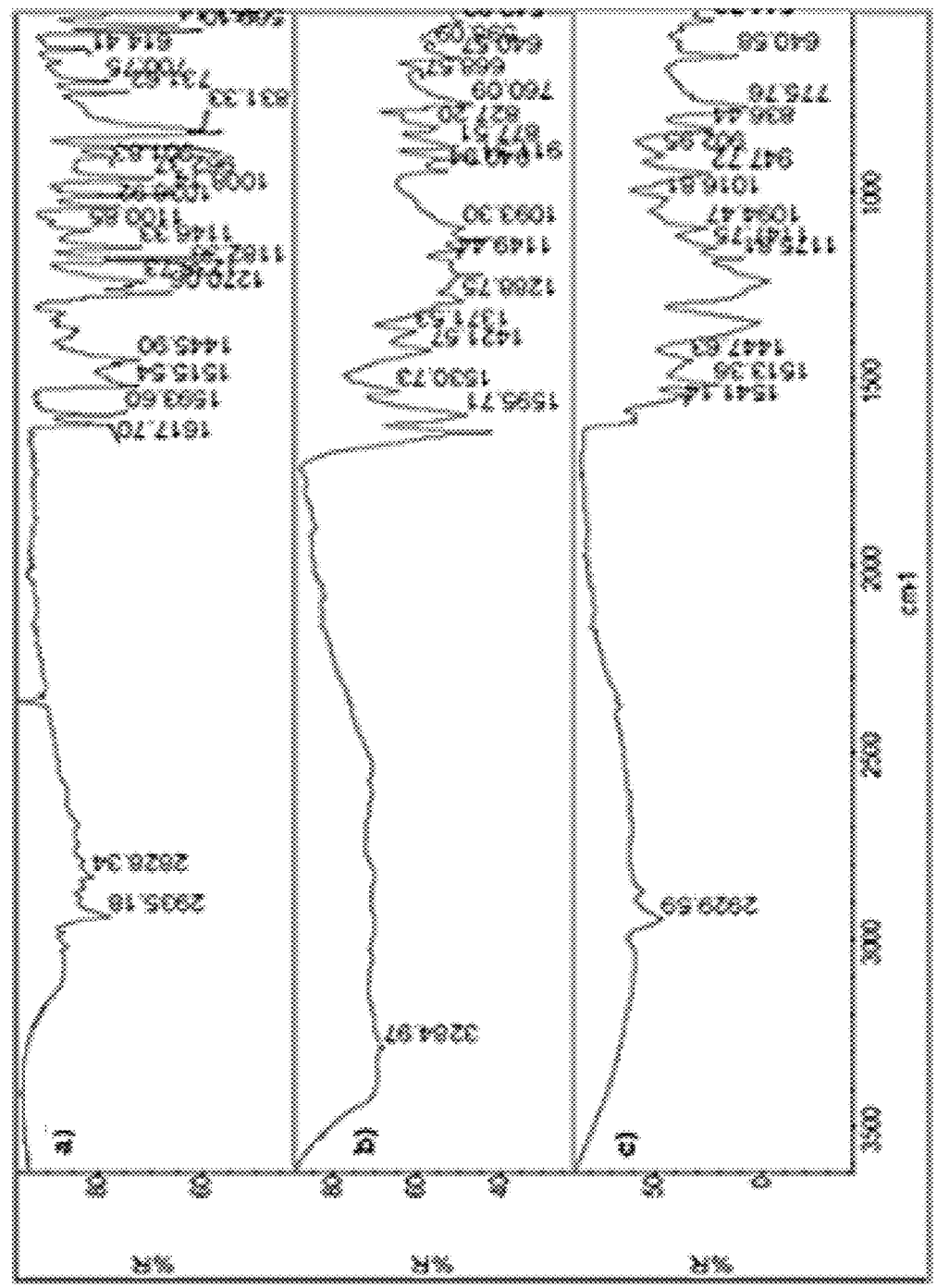
FIG. 1B. IR Spectrum of: a) neutral desvenlafaxine, b) 3,4-dihydroxybenzoic acid, and c) new amorphous solid phase of desvenlafaxine-3,4-dihydroxybenzoic acid.
Figure 1C:
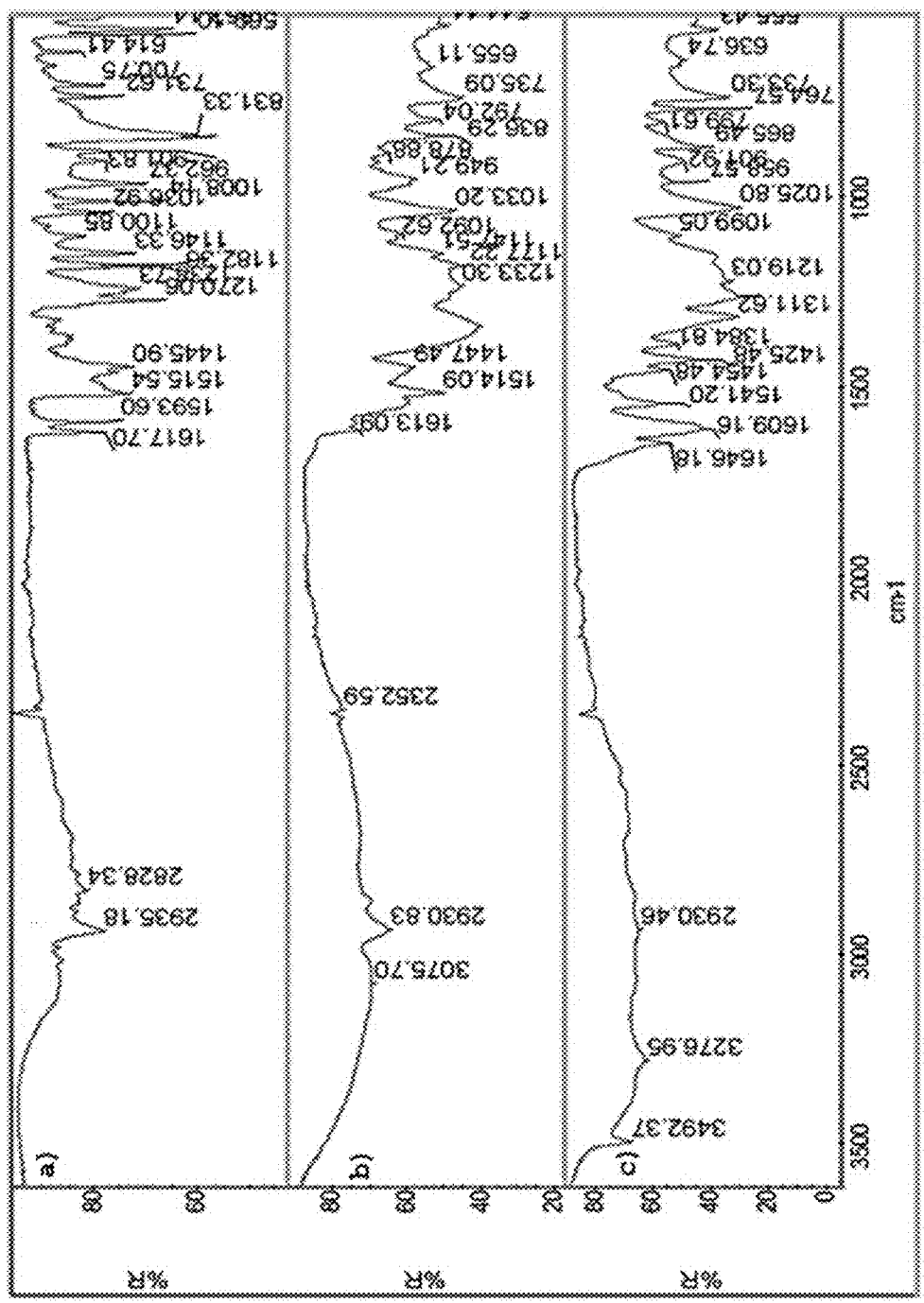
FIG. 1C. IR Spectrum of: a) neutral desvenlafaxine, b) new amorphous solid phase of desvenlafaxine 3,4,5-trihydroxybenzoic acid, and c) 3,4,5-trihydroxybenzoic acid.

IR spectra were obtained for: a) neutral DSV, b) new solid phase (DSV:co-former) and c) the employed co-former. FIGS. 1A, 1B and 1C show IR spectra of the NSF (raw material and product) with 3-hydroxybenzoic acid, 3,4-dihydroxybenzoic acid and 3,4,5-trihydroxybenzoic acid, respectively. For each one of these spectra, letter a) corresponds to the spectrum of neutral desvenlafaxine, letter b) corresponds to the spectrum of the NSF, and letter c) corresponds to the spectrum of the co-former.

As can be observed from FIGS. 1A, 1B and 1C, the infrared spectrum of the NSF is different to the superposition of the spectra of the raw material, but it contains bands that are similar to those of the DSV base and the co-former. In addition, the spectrum corresponding to the NSF contains IR bands that are notably broader than those of the respective crystalline raw material, suggesting the formation of amorphous solids. Band shifts are also observed in the IR spectra, for example, those of the carbonyl group (v C=O) of the co-former, which appear in the 1621-1705 cm-$^1$ region, are shifted to wavelengths of 1548-1614 cm-$^1$. These shifts are characteristic of carboxylates, suggesting the formation of amorphous salts.

Characterization of Amorphous NSF by X-Ray Powder Diffraction (XRPD)

The specifications for the XRPD analysis were: Copper radiation Kα (λ=1.541 Å) with operation voltage of 300 KV and 10 mA.

Figure 2A:
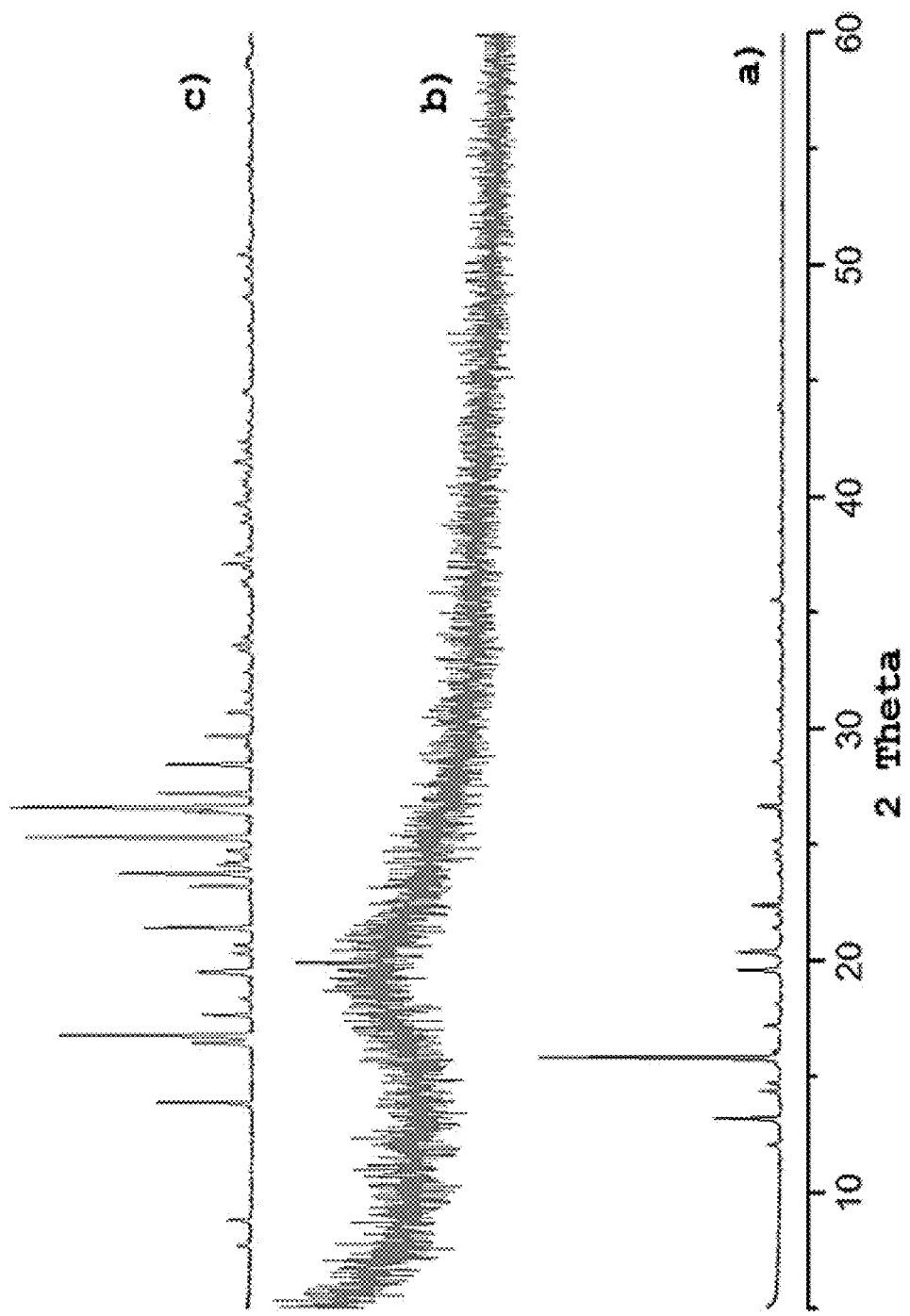
FIG. 2A. X-Ray Diffractograms of: a) neutral desvenlafaxine, b) new amorphous solid phase of desvenlafaxine-3-hydroxybenzoic acid, and c) 3-hydroxybenzoic acid.
Figure 2B:
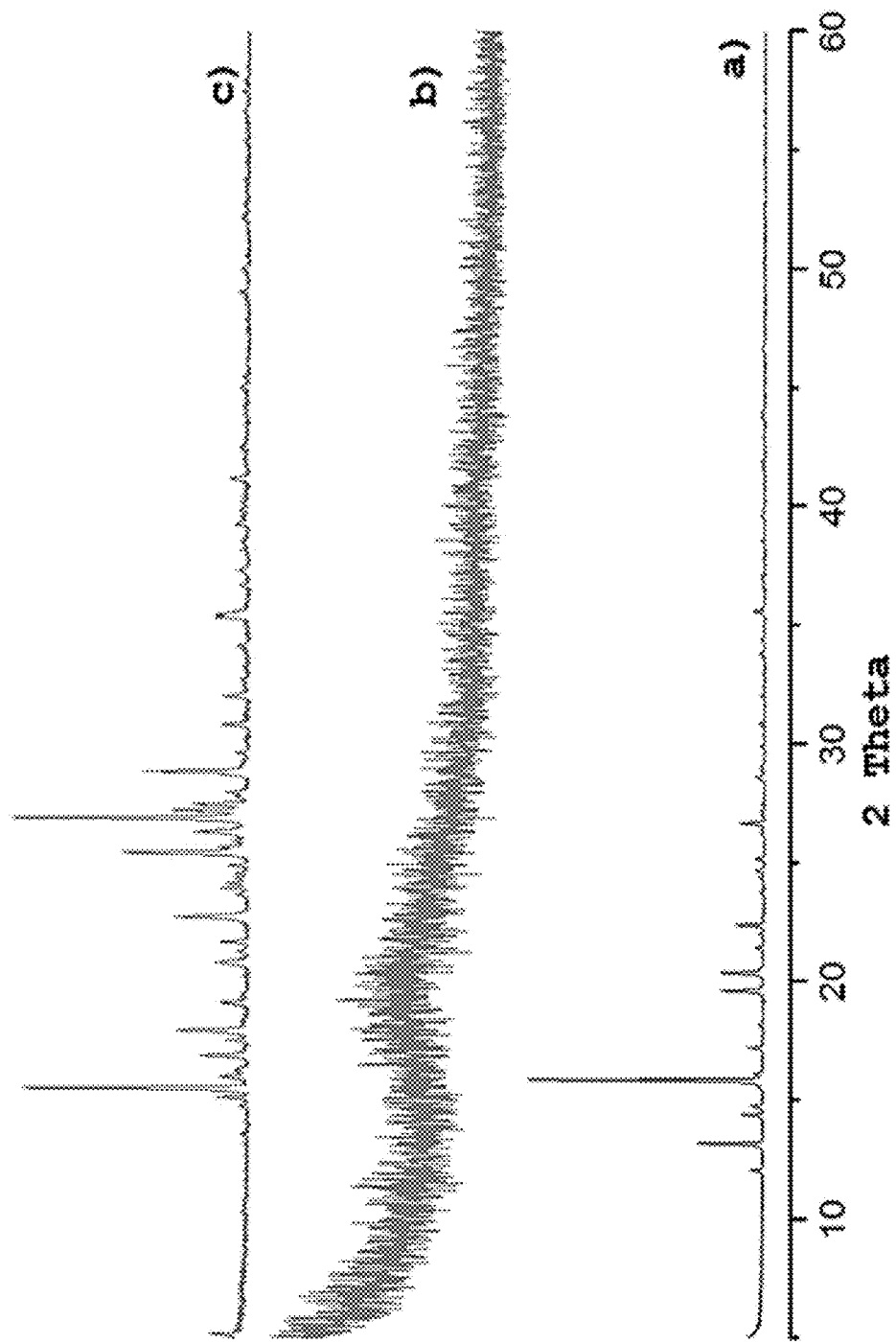
FIG. 2B. X-Ray Diffractograms of: a) neutral desvenlafaxine, b) new amorphous solid phase of desvenlafaxine-3,4-dihydroxybenzoic acid, and c) 3,4-dihydroxybenzoic acid.
Figure 2C:
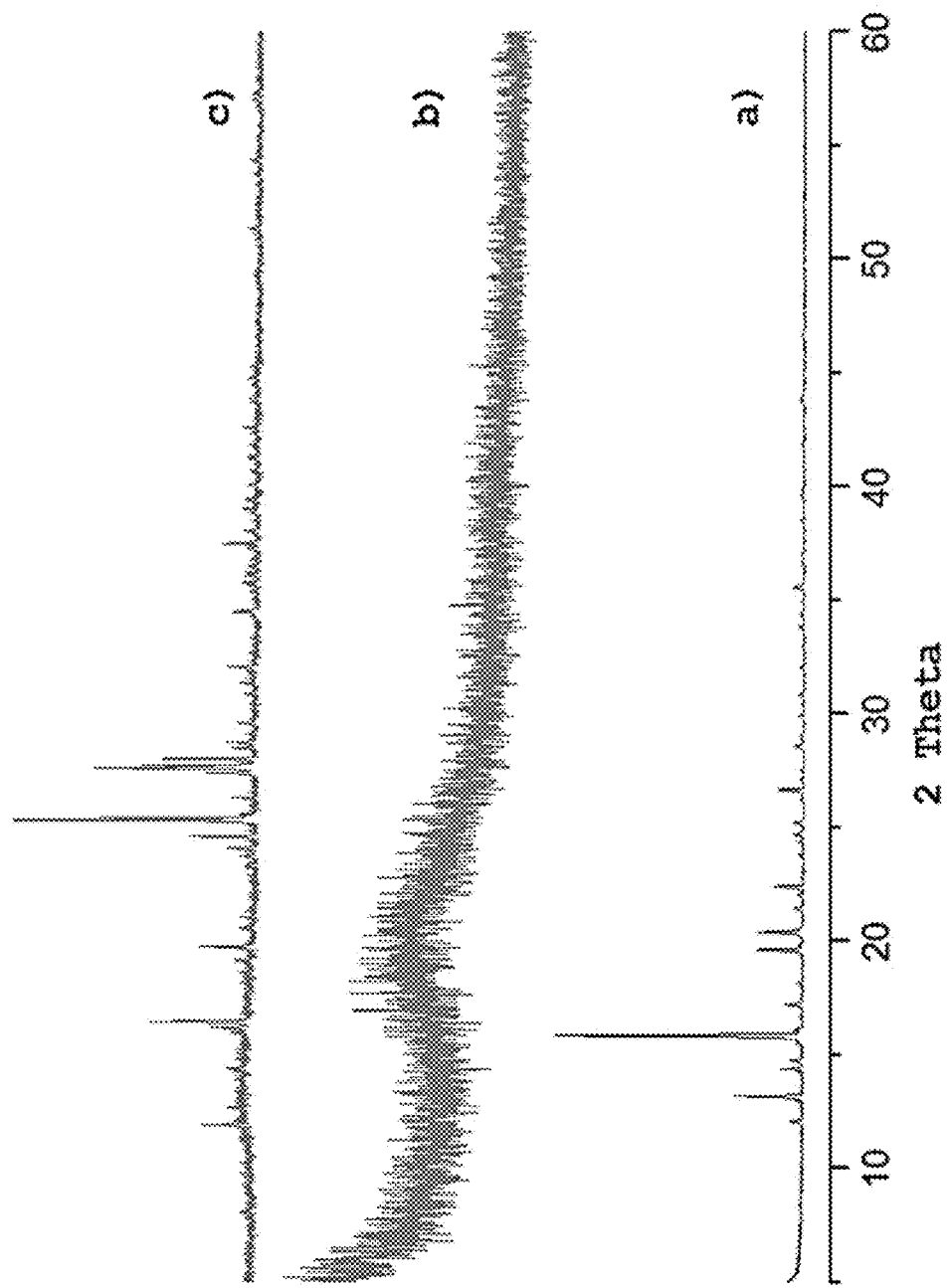
FIG. 2C. X-Ray Diffractograms of: a) neutral desvenlafaxine, b) new amorphous solid phase of desvenlafaxine-3,4,5-trihydroxybenzoic acid, and c) 3,4,5-trihydroxybenzoic acid.

From the performed analysis, the loss of crystallinity in the obtained solids becomes evident, which confirms the formation of amorphous NSF. FIGS. 2A, 2B and 2C show X-Ray diffractograms of the NSF (raw material and product) obtained with 3-hydroxybenzoic acid, 3,4-dihydroxybenzoic acid and 3,4,5-trihydroxybenzoic acid, respectively. For each of these figures, the diffractogram identified with letter a) (lower section of the graph) corresponds to neutral desvenlafaxine; the diffractogram of letter b) (intermediate section of the graph) corresponds to the new solid phase; and the diffractogram of letter c) (upper section of the graph) corresponds to the co-former.

As can be observed from FIGS. 2A-2C, the diffractogram of the NSF is different to the superposition of the spectra of the starting materials, DSV and the co-former.

Characterization of Amorphous NSF by Differential Scanning Calorimetry (DSC) and Thermogravimetric Analysis (TGA)

Figure 3A:
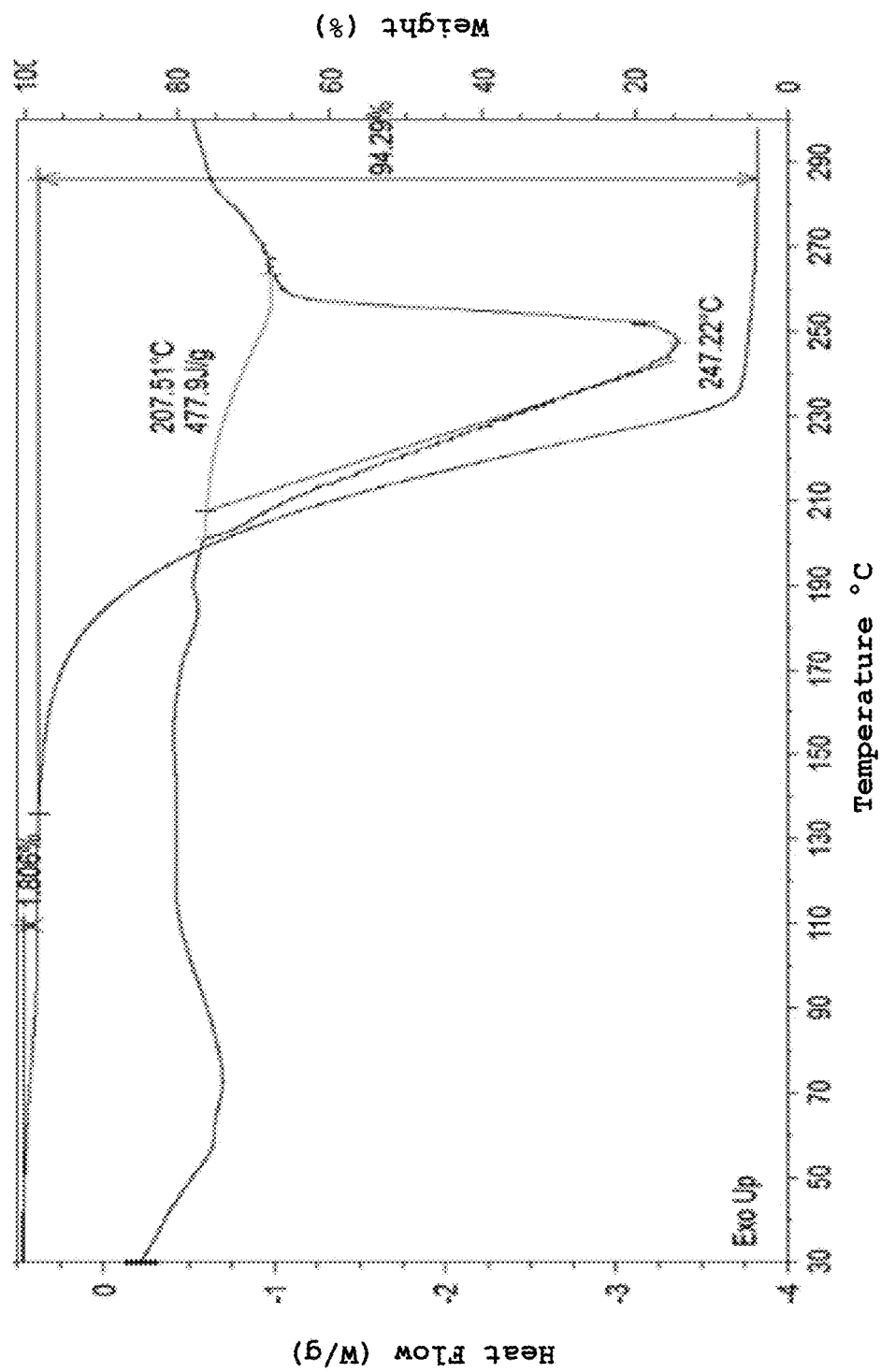
FIG. 3A. DSC-TGA calorimetric analysis of the new amorphous solid phase of desvenafaxine-3-hydroxybenzoic acid.
Figure 3B:
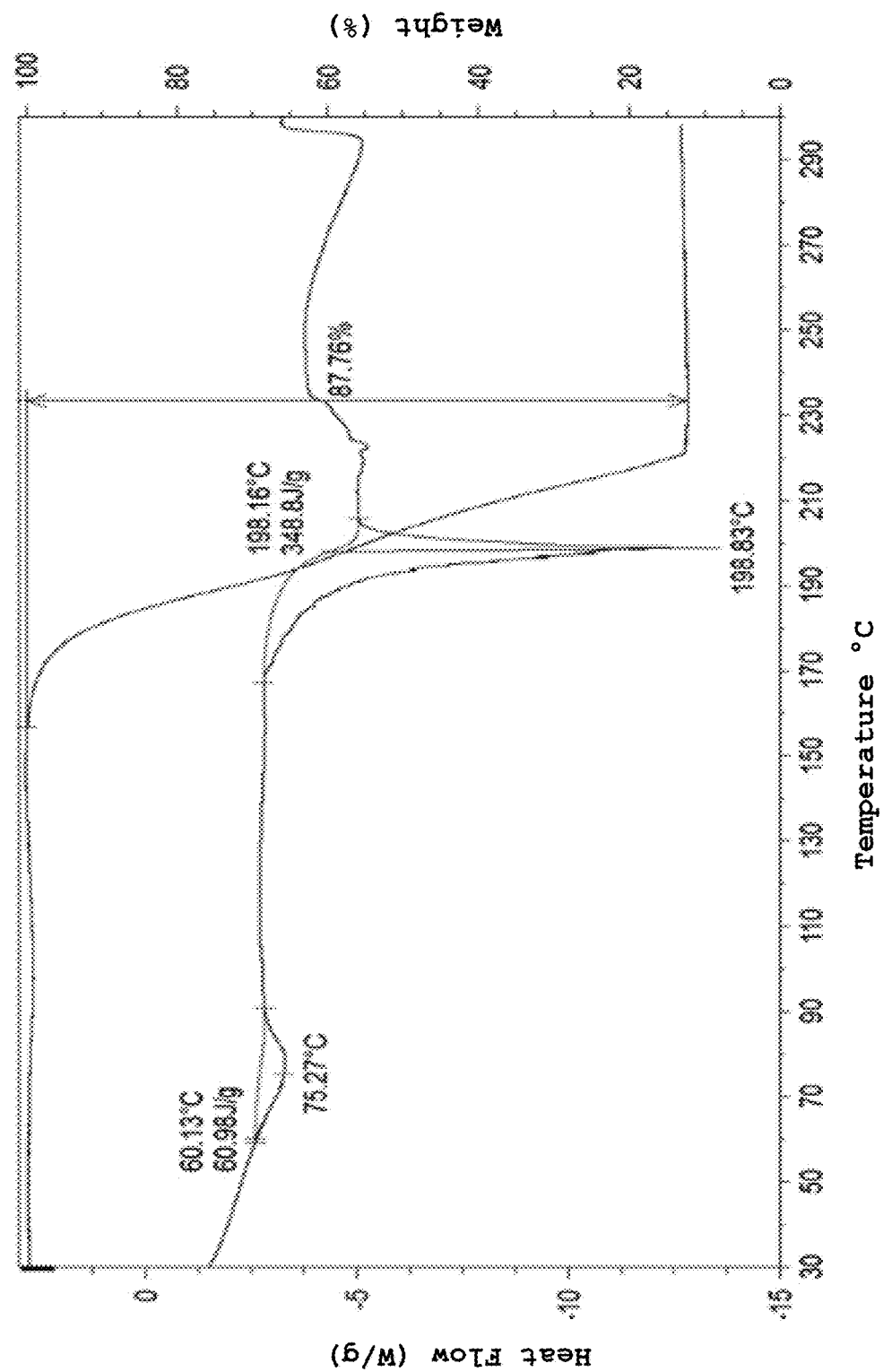
FIG. 3B. DSC-TGA calorimetric analysis of the new amorphous solid phase of desvenafaxine-3,4-dihydroxybenzoic acid.
Figure 3C:
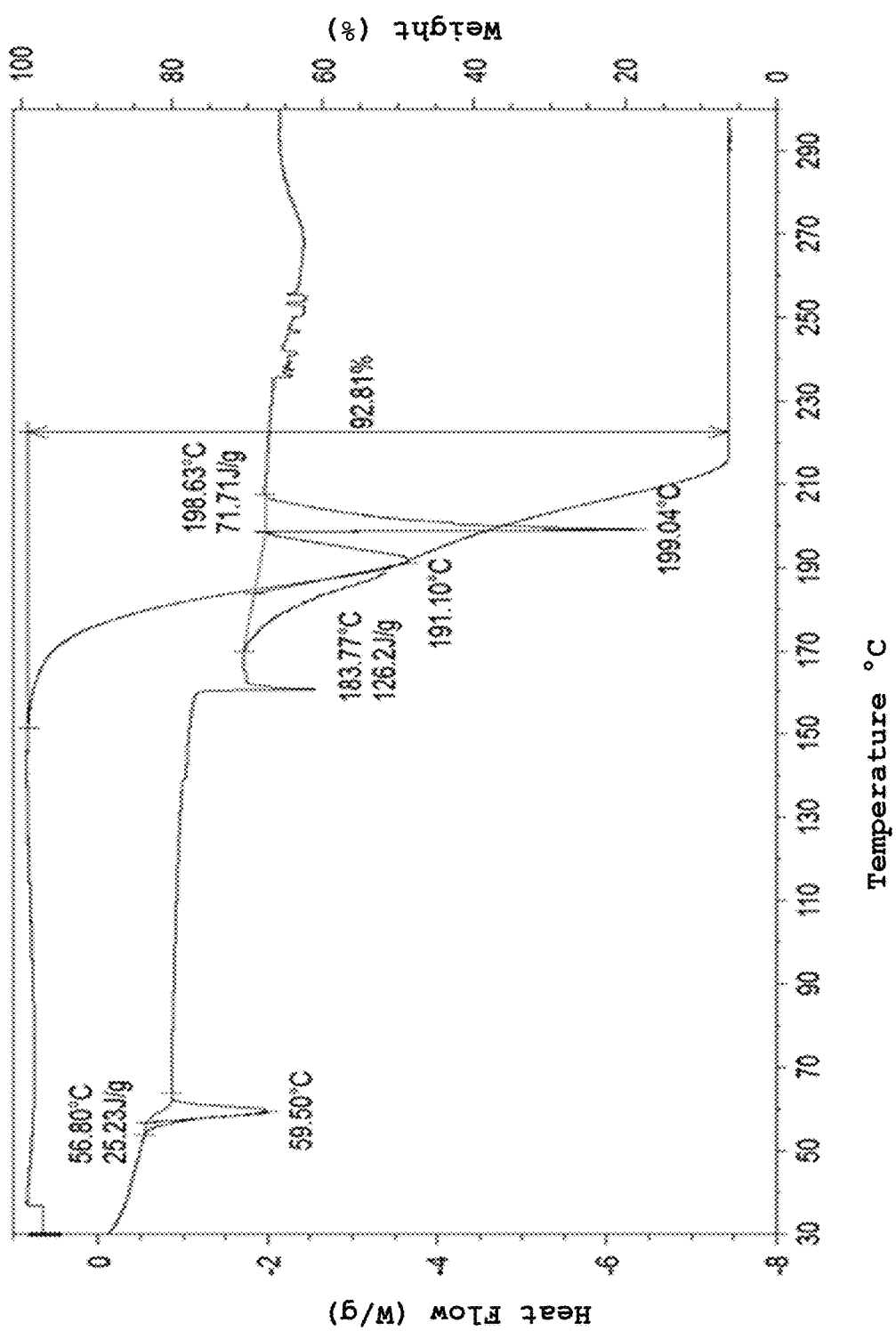
FIG. 3C. DSC-TGA calorimetric analysis of the new amorphous solid phase of desvenafaxine-3,4,5-trihydroxybenzoic acid.

FIGS. 3A, 3B and 3C show the results of the calorimetric analysis DSC-TGA of the NSF with 3-hydroxybenzoic acid, 3,4-dihydroxybenzoic acid and 3,4,5-trihydroxybenzoic acid, respectively. As observed, the DSC analysis shows absence of melting points as reported for amorphous solids. In these cases, glass transitions are observed around 50° C. Neither a crystallization process or melting points are observed. In the TGA analysis a mass loss is observed at about 150° C., which corresponds to the loss of the drug and the co-former.

Solubility and Dissolution Rate Tests of the New Amorphous Solid Form

Solubility tests could not be determined because the amorphous NSF obtained are very soluble and a large amount is required to saturate the solution. For example, from 200 mg to 200 μl of the NSF of DSV:3,4,5-THB were added, and the solution did not become saturated; a dense gel formation was observed, but no precipitate was formed.

The dissolution rate tests were performed in aqueous media, in a Wood apparatus with 150 mg tablets at 37° C. and 50 rpm in different dissolution media, as shown in Tables 2 and 3.

TABLE 2

NSF Dissolution Results

| Dissolution Medium | pH | Range, NSF Dissolution Rate with respect to DSV |
|---|---|---|
| Phosphate buffer | pH 6.8 | 11 to 18 times higher |
| Acetate buffer | pH 4.5 | 4 to 5 times higher |
| HCl buffer | pH 1.2 | 1.2 to 1.5 times higher |

TABLE 3

Dissolution Rate Constants (mg/cm$^2$ · min)

| pH | DSV:3-HB | Amorphous NSF DSV:3,4-DHB/PM* | Amorphous NSF DSV:3,4,5-THB/PM* | DSV |
|---|---|---|---|---|
| 1.2 | 5.8 | 4.4/3.9 | 5.4/3.8 | 6.9 |
| 4.5 | 6.1 | 5.0/2.8 | 6.1/4.3 | 1.2 |
| 6.8 | 5.4 | 5.7/5.0 | 9.0/4.9 | 0.5 |
| water | 3.8 | 2.3 | 1.6 | 0.0 |

*PM. Physical mixture

FIGS. 4A-4I exhibit dissolution rate profiles at different pH values.

Figure 4A:
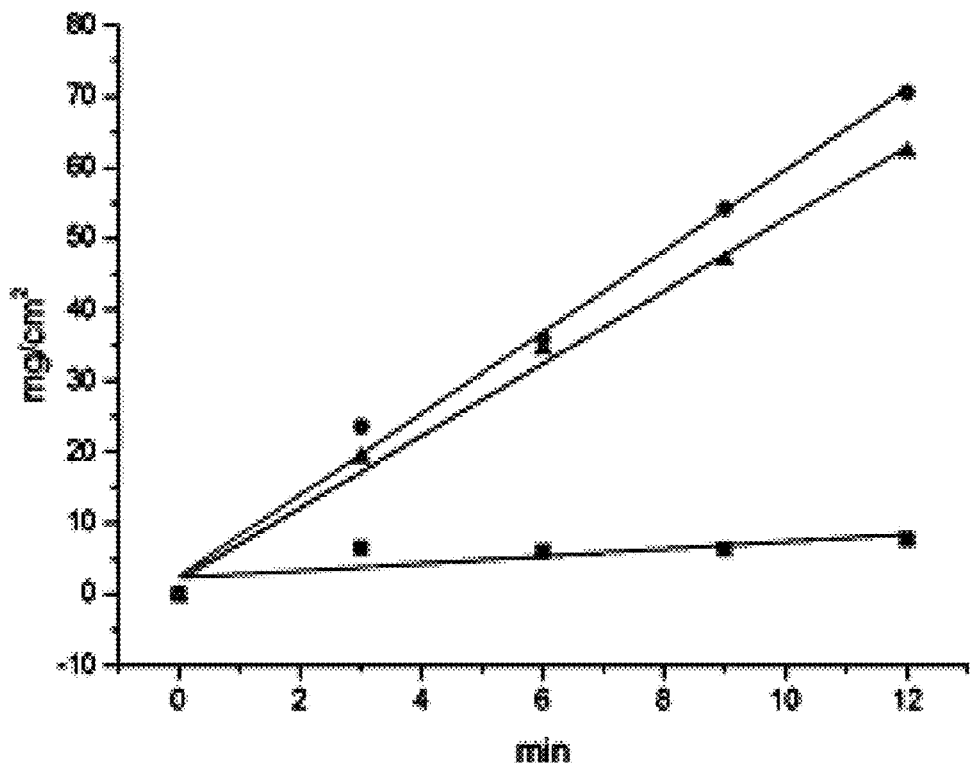
Figure 4B:
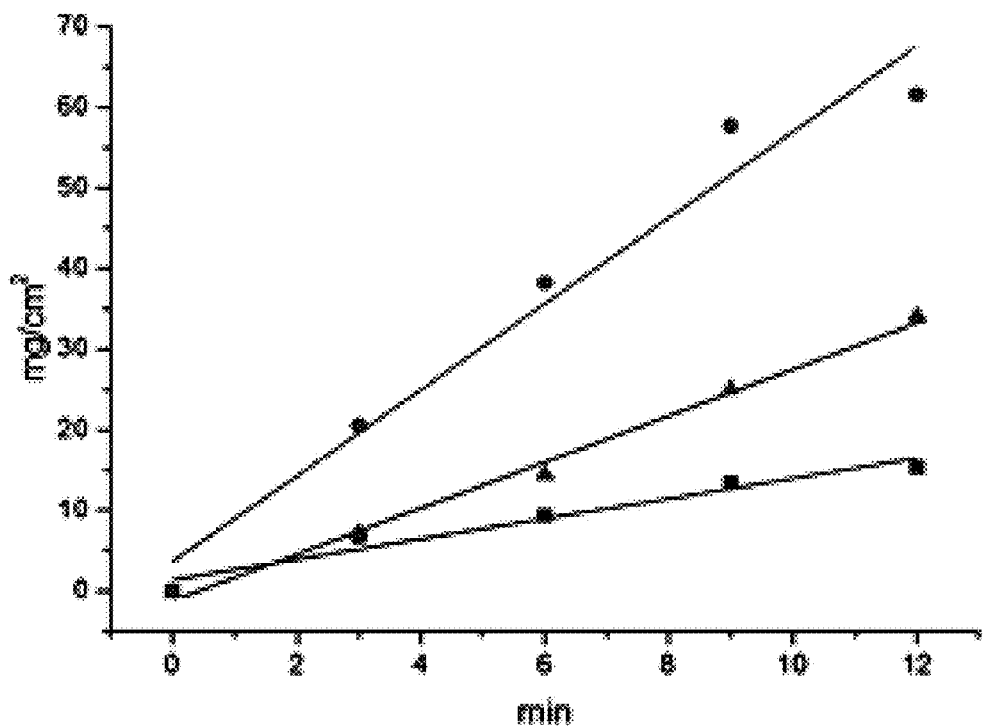
Figure 4C:
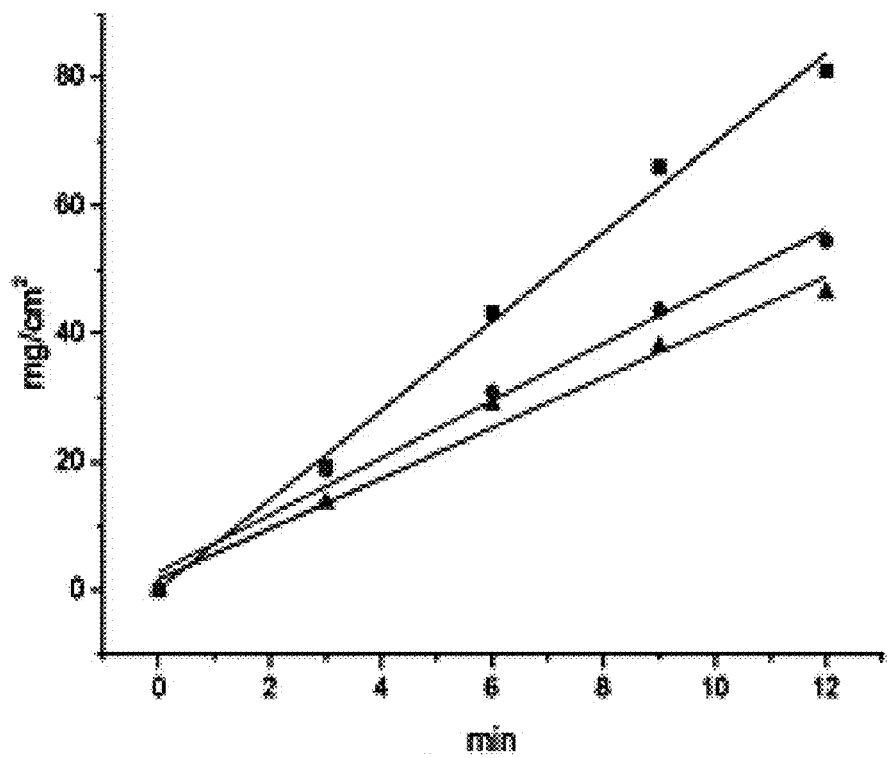

FIGS. 4A-4C exhibit the comparison of dissolution rate profiles in FIG. 4A) phosphate buffer (pH=6.8), FIG. 4B) acetate buffer (pH=4.8) and FIG. 4C) saturated HCl solution (pH=1.2) for desvenlafaxine base (line with squares (■)), the new amorphous solid phase of desvenlafaxine-3,4-dihydroxybenzoic acid (line with circles (●)), and the physical mixture of desvenlafaxine-3,4-dihydroxybenzoic acid (line with triangles (▲)).

Figure 4D:
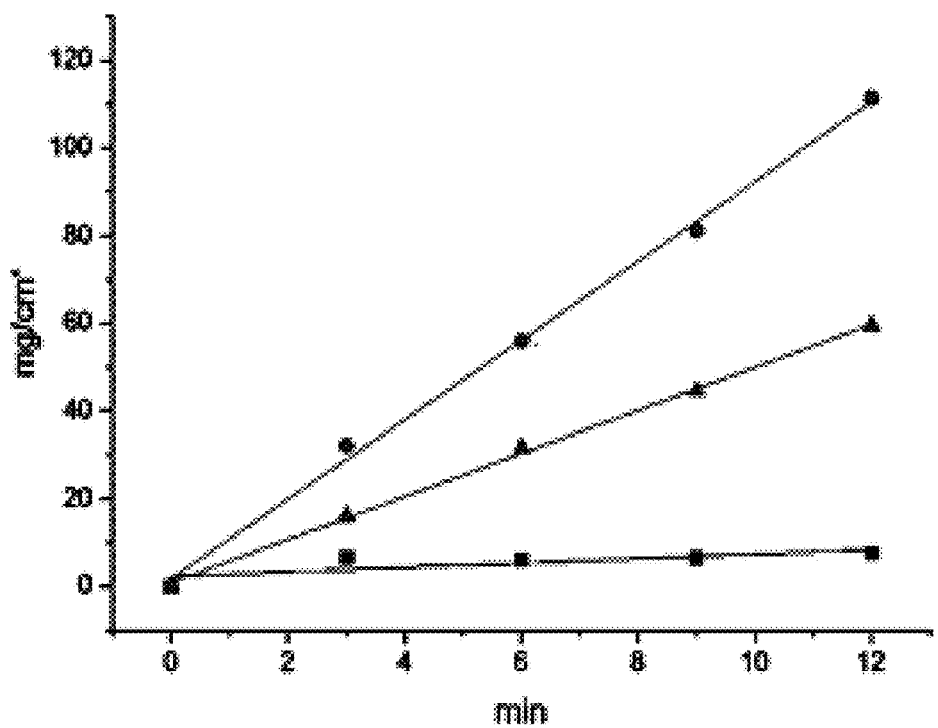
Figure 4E:
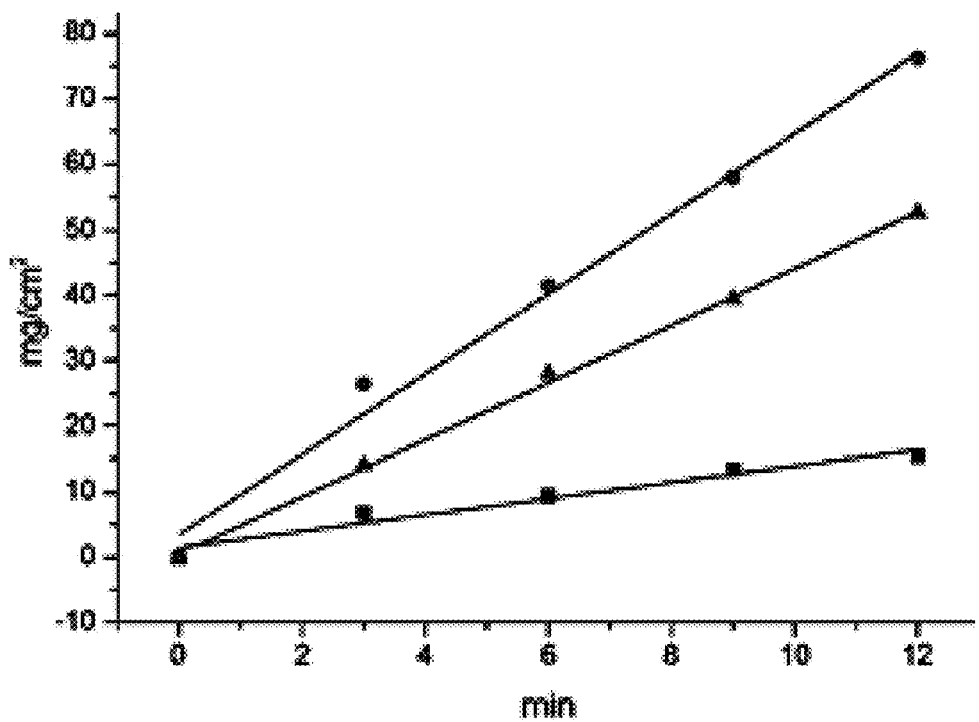
Figure 4F:
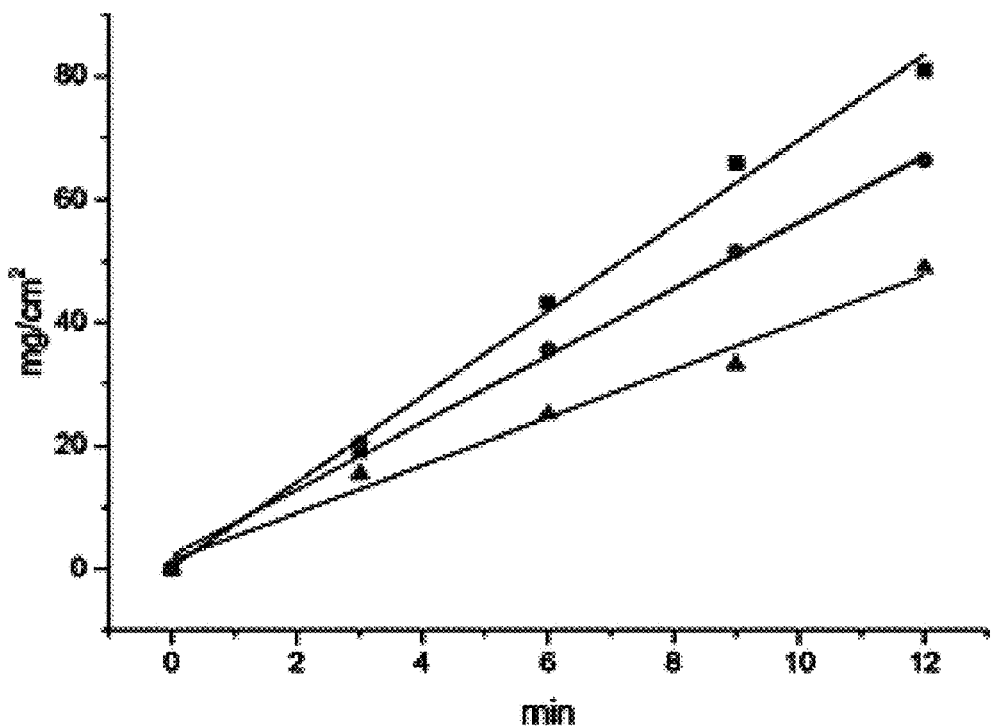

FIGS. 4D-4F exhibits the comparison of the dissolution rate profiles in: FIG. 4D) phosphate buffer (pH=6.8), FIG. 4E) acetate buffer (pH=4.8) and FIG. 4F) saturated HCl solution (pH=1.2) for desvenlafaxine base (line with squares (■)), the new amorphous solid phase of desvenlafaxine-3,4,5-trihydroxybenzoic acid (line with circles (●)), and the physical mixture of desvenlafaxine-3,4,5-Trihydroxybenzoic acid (line with triangles (▲)).

Figure 4G:
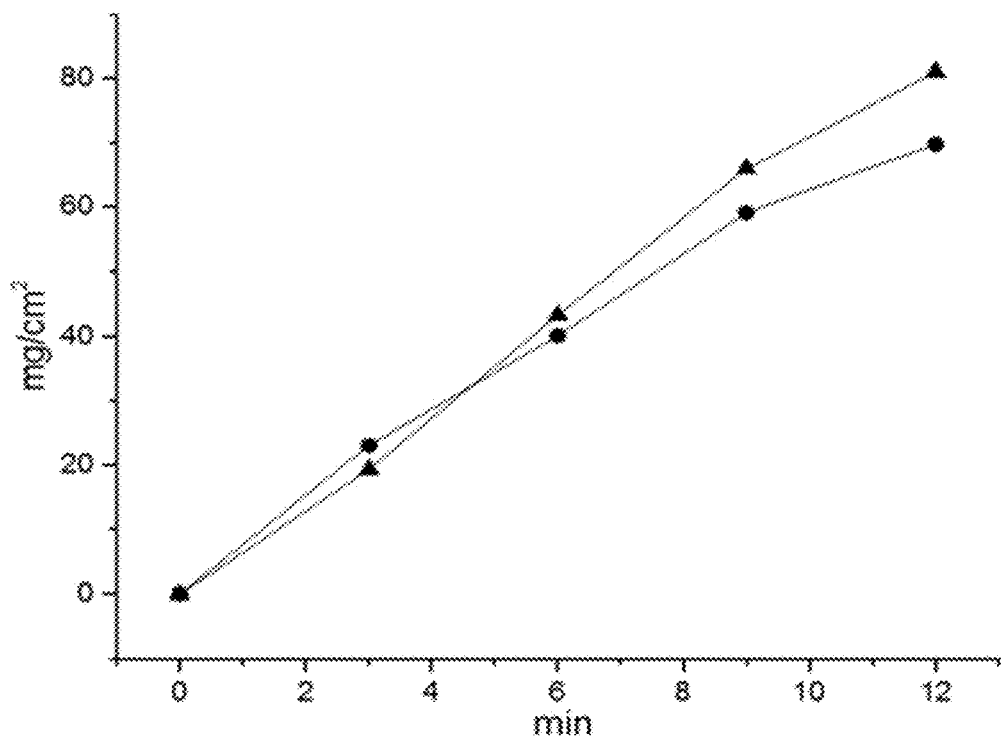
Figure 4H:
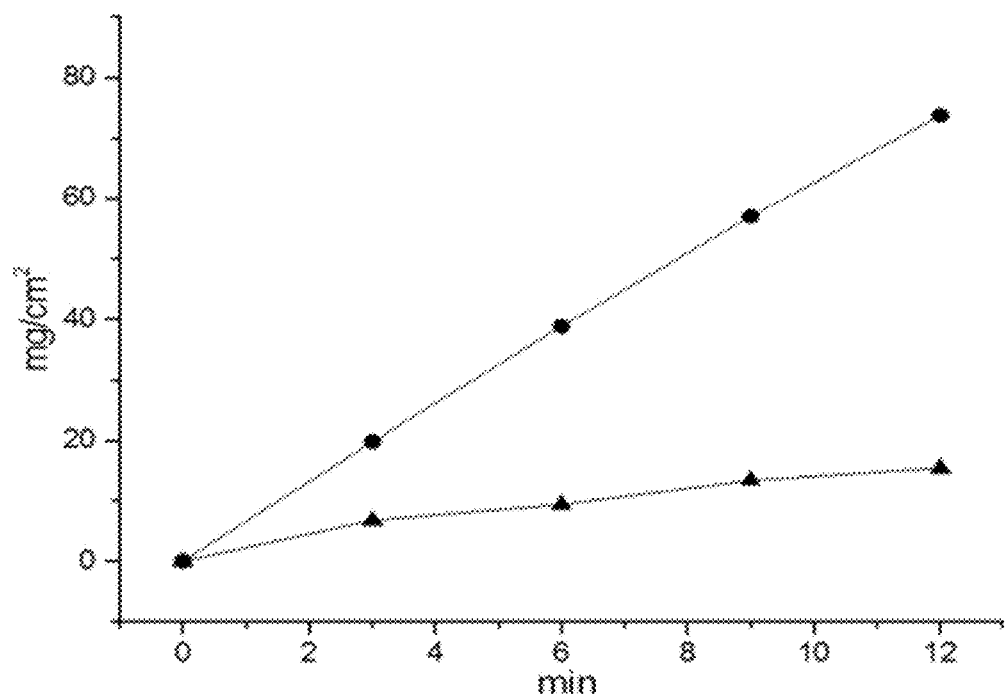
Figure 4I:
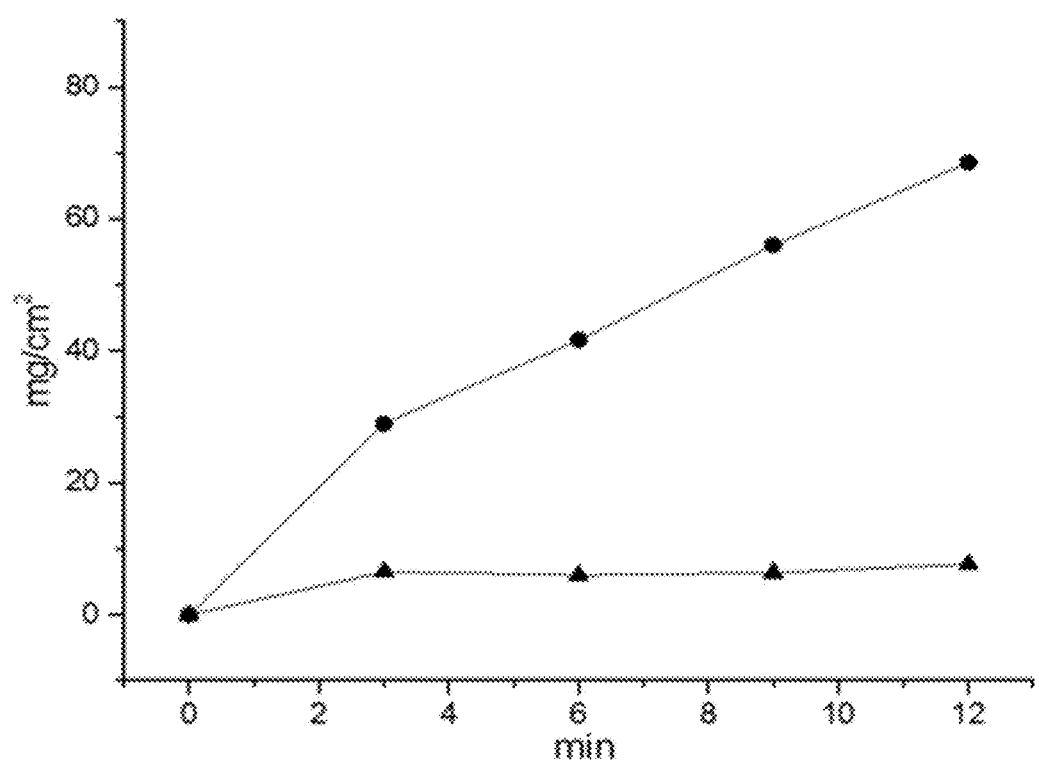

FIGS. 4G-4I show the dissolution rate profiles in: FIG. 4G) phosphate buffer (pH=6.8), FIG. 4H) acetate buffer (pH=4.8) and FIG. 4I) saturated HCl solution (pH=1.2) for the amorphous NSF of desvenlafaxine-3-hydroxybenzoic acid (line with circles (●)) and the physical mixture of desvenlafaxine-3-hydroxybenzoic acid (line with triangles (▲)).

From FIGS. 4A-4I it is observed that the amorphous NSF with 2-hydroxybenzoic acid, 3,4-dihydroxybenzoic acid and 3,4,5-trihydroxybenzoic acid show a higher dissolution rate as compared to the neutral DSV.

During the dissolution rate tests it was observed that DSV has a strong dependency on the pH of the dissolution medium; DSV showed a difference in rate which was 14 times higher in pH 1.2 than in pH 6.8, however the DSV:3,4-DHB NSF presents a lower or almost null difference in the dissolution rates in different dissolution media (FIGS. 4A-4C).

Indicative Physical Stability Tests

The amorphous NSF obtained from DSV:3-HB, DSV:3,4-DHB and DSV:3,4,5-THB were subjected to physical stability tests, wherein the NSF were subjected to temperatures of 45 and 50° C. in dry conditions (no humidity), and to 40° C., 75% humidity for 30 days. The NSF were characterized by X-ray powder diffraction and the diffractograms are shown in FIGS. 5A-5C.

Figures 5A, 5B, 5C:
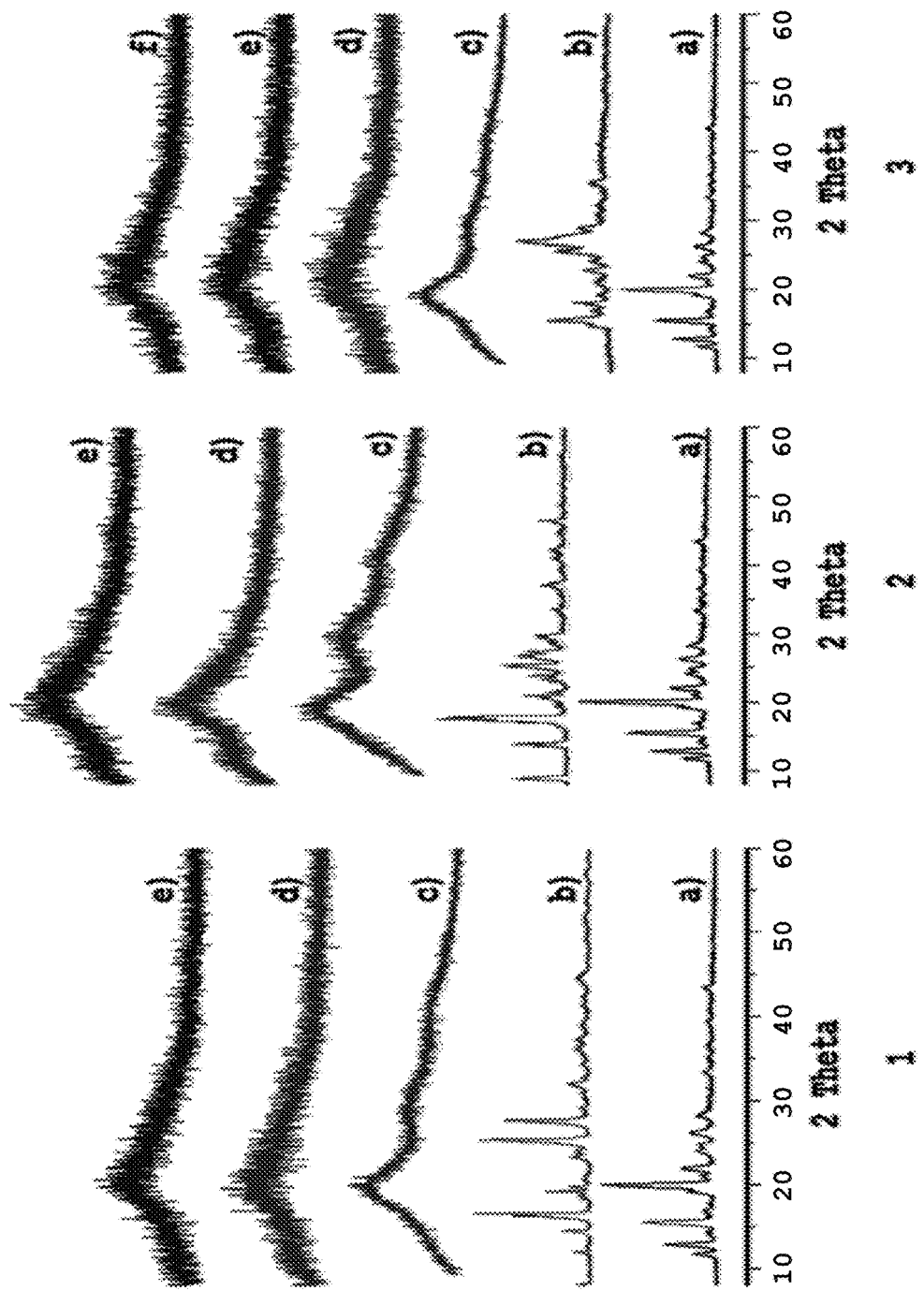
FIG. 5B. Powder diffractograms obtained from the stability test for: a) neutral desvenlafaxine, b) 3-hydroxybenzoic acid co-former, c) initial new amorphous solid phase of desvenlafaxine-3-hydroxybenzoic acid, d) amorphous phase subjected to 45° C. in dry conditions and e) amorphous phase subjected to 50° C. in dry conditions.
FIG. 5C. Powder diffractograms obtained from the stability test for: a) neutral desvenlafaxine, b) co-former 3,4-dihydroxybenzoic acid, c) initial new amorphous solid phase of desvenlafaxine-3,4-dihydroxybenzoic acid, d) amorphous phase subjected to 45° C. in dry conditions, e) amorphous phase subjected to 50° C. in dry conditions, and f) amorphous phase subjected to 40° C. with 75% relative humidity.

FIG. 5A shows the powder diffractograms obtained from the stability test for: a) desvenlafaxine base; b) co-former 3,4,5-THB; c) initial DSV:3,4,5-THB NSF; d) DSV:3,4,5-THB NSF subjected to 45° C. in dry conditions; and e) DSV:3,4,5-THB NSF subjected to 50° C. in dry conditions.

FIG. 5B shows the powder diffractograms obtained from the stability test for: a) desvenlafaxine base; b) co-former 3-HB; c) initial DSV:3-HB NSF; d) DSV:3-HB NSF subjected to 45° C. in dry conditions; and e) DSV:3-HB NSF subjected to 50° C. in dry conditions.

FIG. 5C shows the powder diffractograms obtained from the stability test for: a) desvenlafaxine base; b) co-former 3,4-DHB; c) initial DSV:3,4-DHB NSF; d) DSV:3,4-DHB NSF subjected to 45° C. in dry conditions; e) DSV:3,4-DHB NSF subjected to 50° C. in dry conditions; and f) DSV:3,4-DHB NSF subjected to 40° C. with 75% relative humidity.

From the samples subjected to 40° C. and 75% humidity, it was only possible to characterize the DSV:3,4-DHB NSF by X-ray diffraction (FIG. 5C), because the other solid forms became hydrated. For this reason, FIGS. 5A and 5B do not show the corresponding spectra.

Figure 6A:
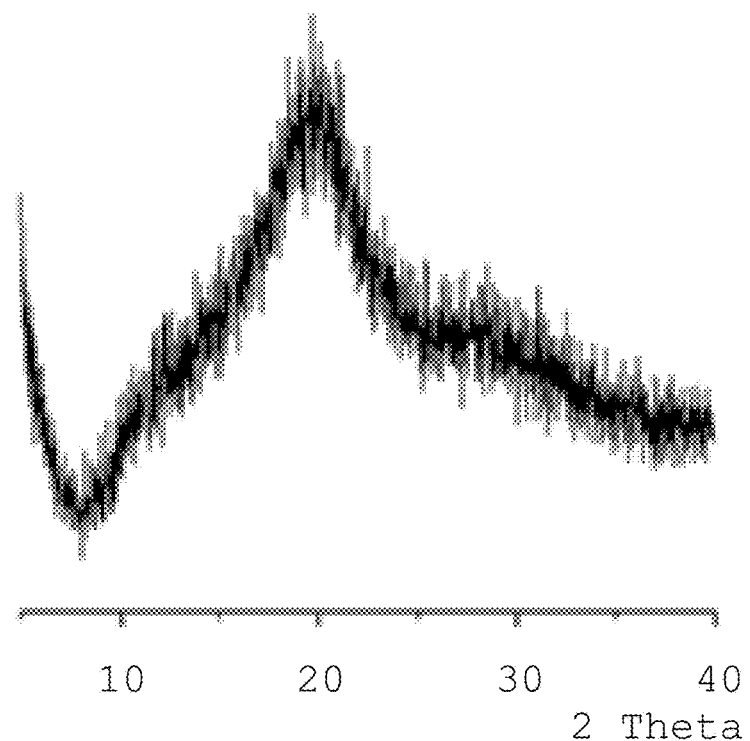
FIG. 6A. X-Ray powder diffractogram of the new amorphous solid phase of desvenlafaxine-3,4,5-trihydroxybenzoic acid obtained in methanol.
Figure 6B:
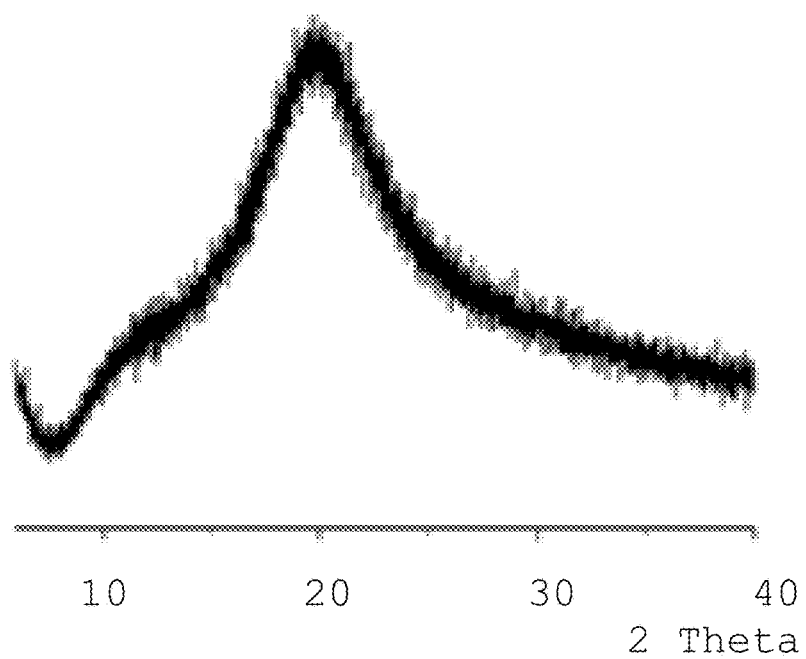
FIG. 6B. X-Ray powder diffractogram of the new amorphous solid phase of desvenlafaxine-3,4,5-trihydroxybenzoic acid obtained in ethanol.

We verified that the same phase was obtained using ethanol as the dissolution medium, as an alternative to methanol. FIGS. 6A y 6B show X-ray powder diffractograms of the new amorphous solid form DSV-3,4,5-THB obtained in methanol and ethanol, respectively. These graphs allow confirming the reproducibility of the processes for obtaining the DSV-3,4,5-THB NSF.

New Crystalline Solid Phases

The present invention discloses crystalline NSF formed from DSV and a co-former X, wherein X possesses one or several hydroxyl groups and a carboxyl group and it can form the new entity through ionic interactions or intermolecular forces such as hydrogen bonding and/or van der Waals' links; as well as solvates, hydrates and/or polymorphs of DSV:X. Co-former X is selected from: 2-HB, 3-HB, 4-HB, 2,3-DHB, 2,4-DHB, 2,5-DHB, 2,6-DHB, 3,4-DHB, 3,5-DHB, and 3,4,5-THB.

The following is a non-limitative example of the process for obtaining the new crystalline solid forms.

a) Dissolve DSV with the co-former, for example 3,4-DHB, in a 1:1 stoichiometric relation, in a polar solvent selected from ethanol, ethanol 96° C., acetone and mixtures thereof.
b) Place the mixture in a flask with agitation means, for example, propellers, blades or the similar, heating in water bath at 60° C. for 20-30 minutes until obtaining a homogeneous solution.
c) Once the mixing time is finalized, the solvent is evaporated under vacuum maintaining constant agitation (140 rpm) and heating between 65 and 70° C. The drying time is of between 4 and 6 hours.

The mentioned process was used for producing different amounts of 3,4-DHB NSF, 2.5 g, 5 g, 10 g and 100 g, among other amounts.

Synthesis of the Crystalline NSF of DSV by Using the Slurry Method

We carried out variations to the method of synthesizing the new crystalline solid form with 3,4-DHB, by using the slurry method. For this purpose, we started with a mixture of DSV and 3,4-DHB (stoichiometric proportion 1:1) with small amounts of polar solvent (for example, 5 mL ethanol 96%) under agitation (for example 150 rpm) at room temperature.

The reaction system was carried out with a three-necked flask (closed system). After 6 hours of agitation under the mentioned conditions, the remaining solvent was eliminated under vacuum for a period of 4 hours, maintaining a bath at a temperature of 50° C. During the reaction time, samples of the solid mixture were taken at the following time points: 30 min, 1 h, 2 h, 6 h. The NSF was detected as complete since the 30 minutes from the initiation of the reaction. Based on the above, a reaction time of 2 hours was established.

The developed preparation processes were reproduced for obtaining 2.5 g, 5 g, 10 g and higher amounts. The solid obtained in the scaling reactions corresponds to the crystalline phase as the 3,4-dihydroxybenzoate salt of anhydrous desvenlafaxine.

Figure 7:
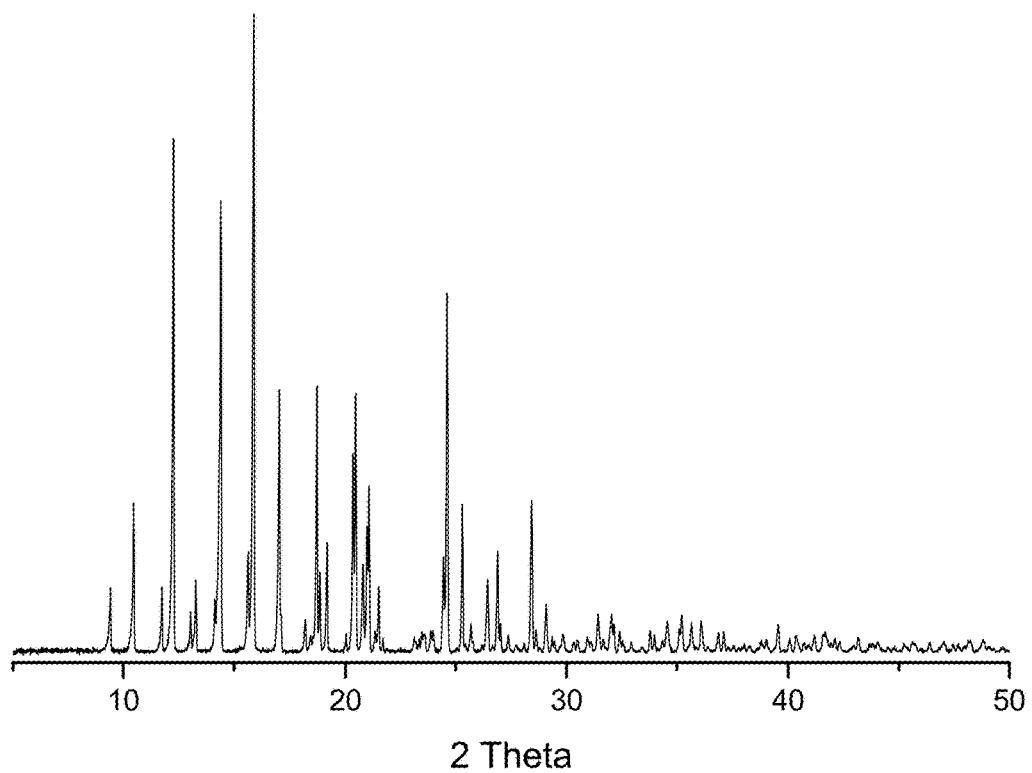
FIG. 7. X-Ray powder diffractogram of the new crystalline solid phase of desvenlafaxine-3,4-dihydroxybenzoic acid.

Results and Characterization of the New Crystalline Solid Forms DSV:3,4-DHB and DSV:2,4-DHB The crystalline NSF of DSV:3,4-DHB was subjected to recrystallization in ethanol 96%, obtaining monocrystals that were useful for X-ray diffraction study. From this analysis, it was possible to elucidate the molecular structure of the solid (FIG. 7).

Figure 8:
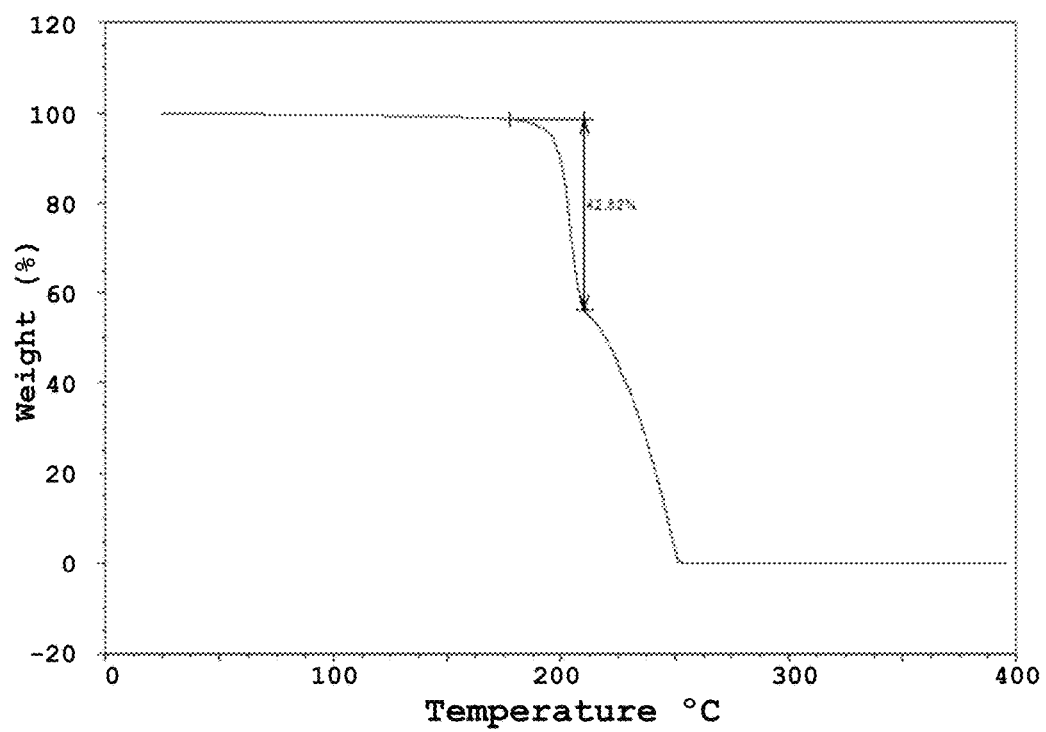
FIG. 8. Thermogravimetric analysis of the new crystalline solid phase of desvenlafaxine-3,4-dihydroxybenzoic acid.

A thermogravimetric analysis (TGA/DSC) of the crystalline NSF DSV:3,4-DHB is shown in FIG. 8. The compound was observed as stable until 190° C., the temperature at which decomposition starts to occur.

Figure 9:
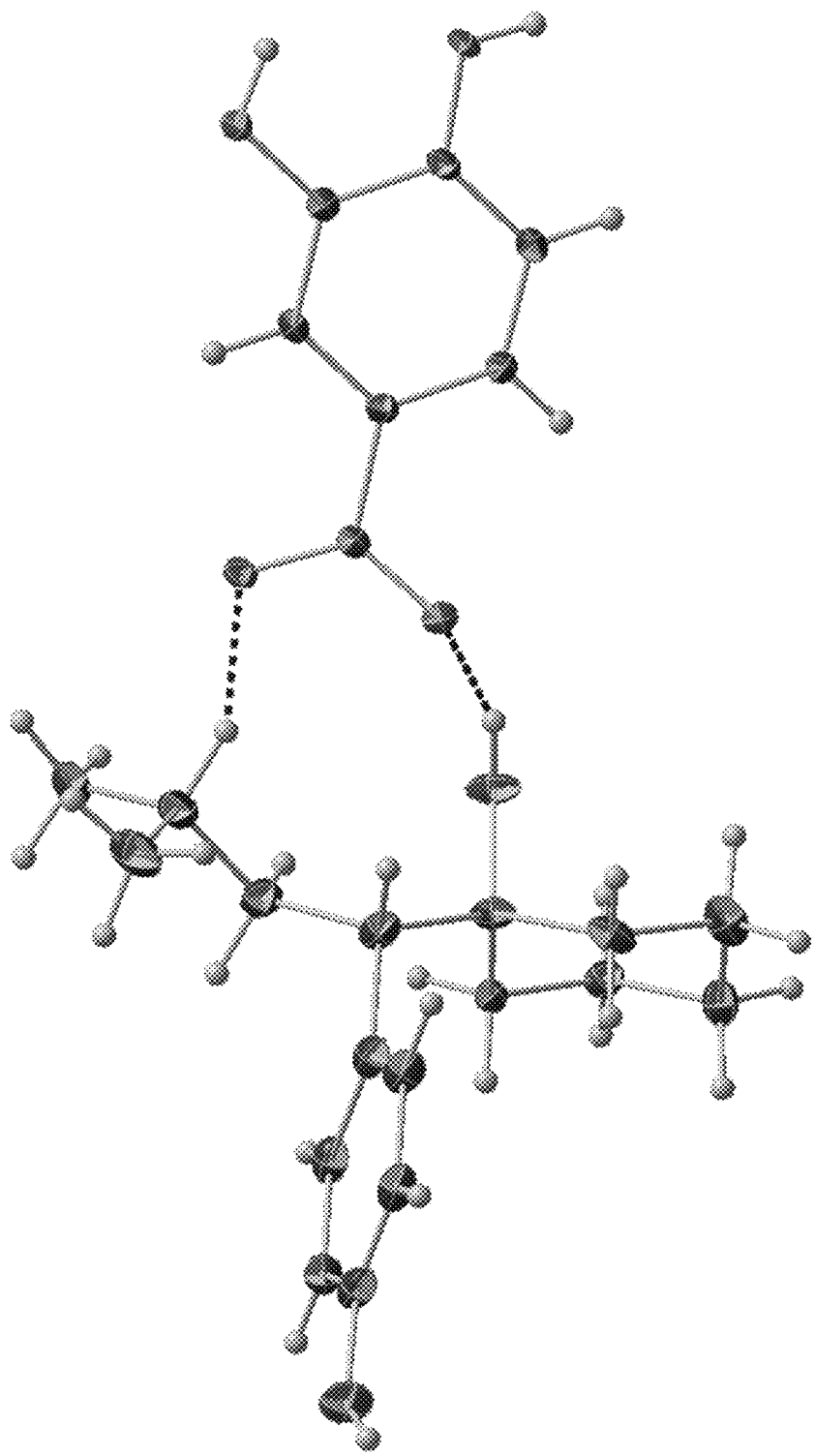
FIG. 9. Crystalline structure obtained by single-crystal X-ray diffraction of the new crystalline solid phase of desvenlafaxine-3,4-dihydroxybenzoic acid.

FIG. 9 exhibits the molecular structure of the new crystalline solid phase of Desvenlafaxine:3,4-dihydroxybenzoic acid, obtained by X-ray powder diffraction. The specifications of the employed diffractometer are: $\lambda_{CuK\alpha1}$=1.5406 Å, germanium monochromator, operated at 40 kV and 40 mA.

Table 4 shows the parameters of the structure obtained by single-crystal X-ray diffraction of the crystalline Desvenlafaxine-3,4-dihydroxybenzoic acid NSF.

TABLE 4

Crystalline structure data for the Desvenlafaxine – 3,4-dihydroxybenzoic acid NSF

| | |
|---|---|
| Empirical formula | C23H31NO6 |
| Molecular weight | 417.49 |
| Temperature/K | 100.02 (11) |
| Crystalline system | monoclinic |
| Spatial group | P21/c |
| a/Å | 18.9712 (6) |
| b/Å | 9.4590 (2) |
| c/Å | 12.5758 (4) |
| α/° | 90 |
| β/° | 98.687 (3) |
| γ/° | 90 |
| Volume/Å$^3$ | 2230.82 (11) |
| Z | 4 |
| ρ calc, g/cm | 1.243 |
| μ/mm$^{-1}$ | 0.732 |
| F(000) | 896.0 |
| Crystal size/mm$^3$ | 1.0 × 0.8 × 0.15 |
| Radiation | CuK$_\alpha$ (λ = 1.54184) |
| 2Θ range for the collection/° | 9.432 to 145.63 |
| Interval indexes | 23 ≤ h ≤ 23, −11 ≤ k ≤ 11, −12 ≤ l ≤ 15 |
| Collected reflections | 15105 |
| Independent reflections | 4391 [Rint = 0.0672, Rsigma = 0.0404] |
| Data/restrictions/parameters | 4391/0/293 |
| Goodness of fit over F2 | 1.067 |
| Final R Indexes [I >= 2σ (I)] | R1 = 0.0982, wR2 = 0.2337 |
| Final R Indexes [all data] | R1 = 0.1023, wR2 = 0.2360 |
| Higher difference of peak/orifice/e Å$^{-3}$ | 0.79/−0.48 |

Figure 10:
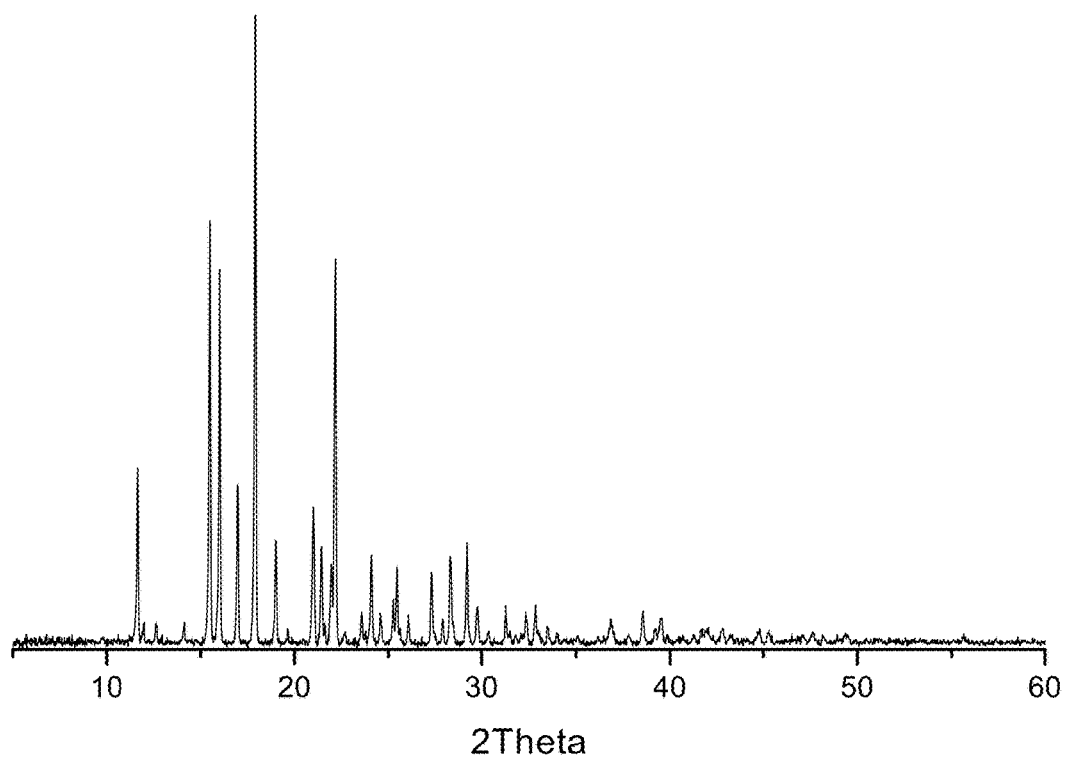
FIG. 10. X-ray diffractogram of the new crystalline solid phase of desvenlafaxine-2,4-dihydroxybenzoic acid.
Figure 11:
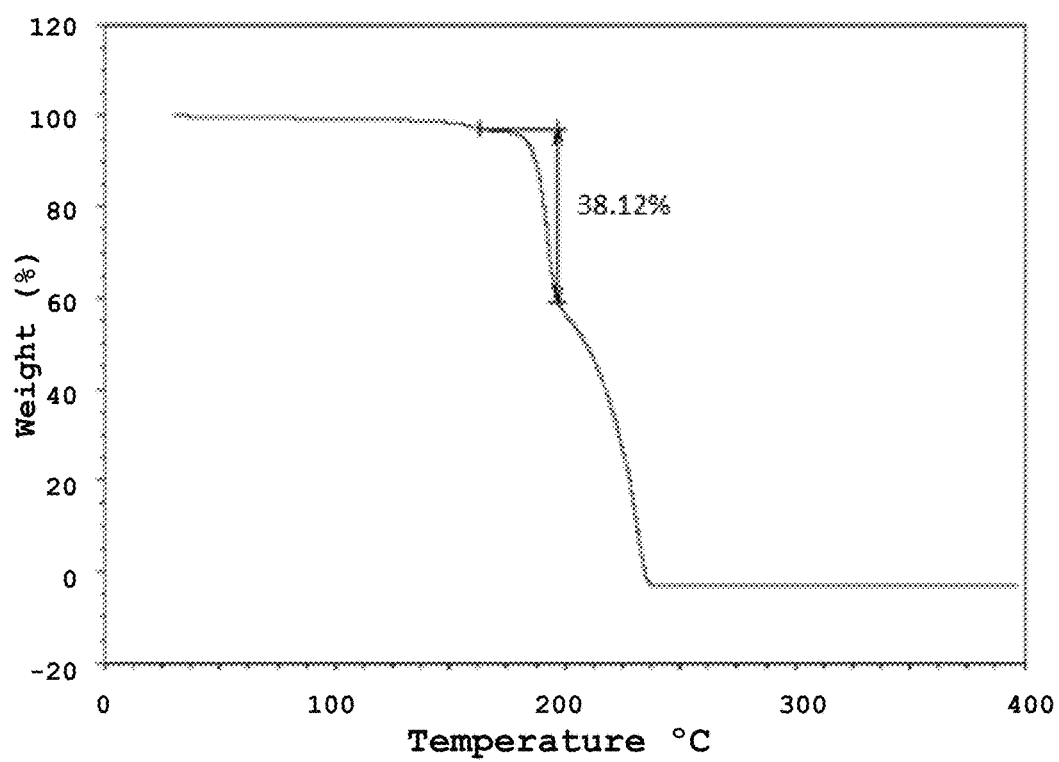
FIG. 11. Thermogravimetric analysis of the new crystalline solid phase of desvenlafaxine-2,4-dihydroxybenzoic acid.

The crystalline NSF of DSV:2,4-DHB was also characterized by X-ray powder diffraction (see FIG. 10), as well as thermogravimetric analysis (TGA/DSC) (see FIG. 11). The thermogravimetric analysis (TGA/DSC) showed that the compound is stable until about 150° C., the temperature at which decomposition starts to occur.

Figure 12:
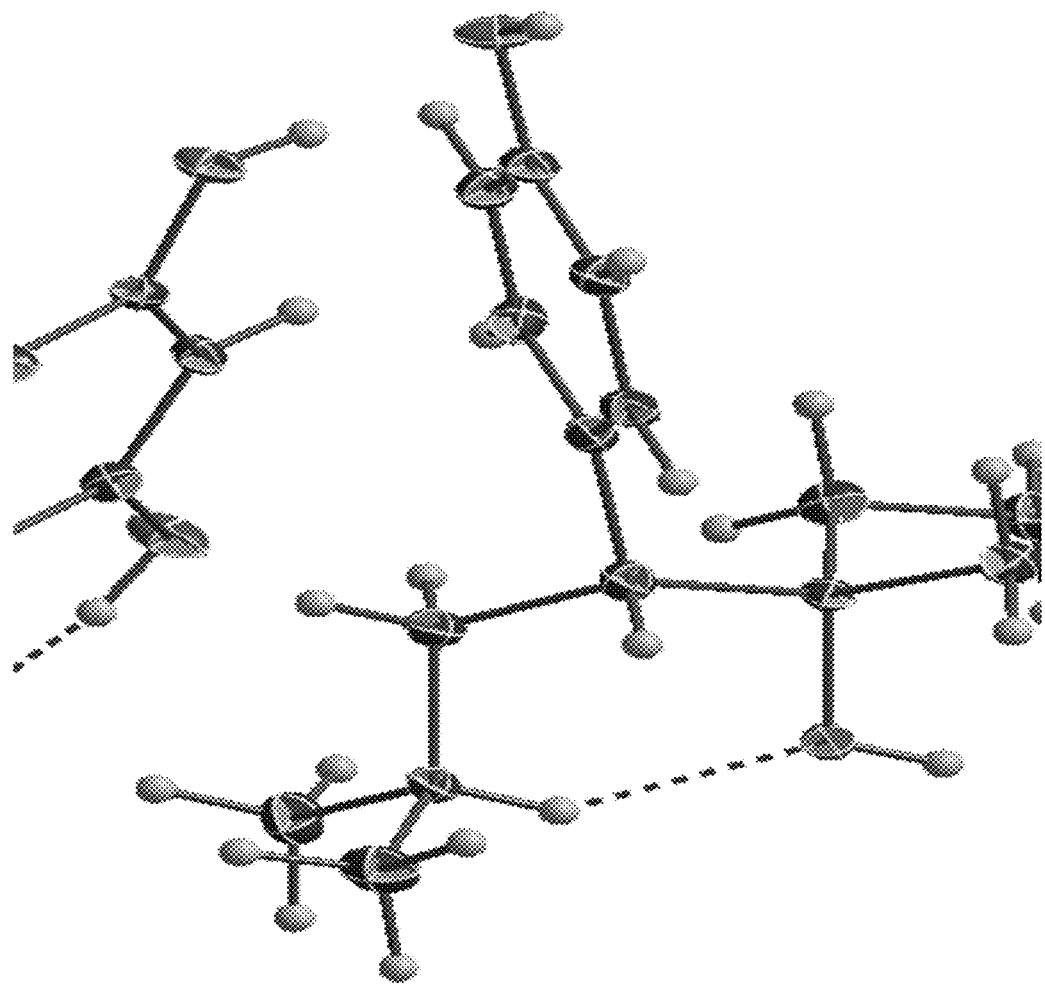
FIG. 12. Crystalline structure obtained by single-crystal X-ray diffraction of the new crystalline solid phase of desvenlafaxine-2,4-dihydroxybenzoic acid.

FIG. 12 exhibits the crystalline structure obtained by single-crystal X-ray diffraction for the new crystalline solid phase of desvenlafaxine-2,4-dihydroxybenzoic acid.

Table 5 shows the parameters of the structure obtained by single-crystal X-ray diffraction of the crystalline NSF desvenlafaxine-2,4-dihydroxybenzoic acid.

TABLE 5

Structural data of the crystalline NSF of Desvenlafaxine – 2,4-dihydroxybenzoic acid

| | |
|---|---|
| Empirical formula | C23H31NO6 |
| Molecular weight | 417.49 |
| Temperature/K | 99.99 (10) |
| Crystalline system | orthorhombic |
| Spatial group | Pna21 |
| a/Å | 18.0299 (3) |
| b/Å | 8.69253 (13) |
| c/Å | 13.86218 (17) |
| α/° | 90 |
| β/° | 90 |
| γ/° | 90 |
| Volume/Å$^3$ | 2172.56 (5) |
| Z | 4 |
| ρ calc, g/cm | 3 1.276 |
| μ/mm$^{-1}$ | 0.752 |
| F(000) | 896.0 |
| Crystal size/mm$^3$ | 0.5 × 0.3 × 0. |
| Radiation | CuK$_\alpha$ (λ = 1.54184) |
| 2Θ range for the collection/° | 9.812 a 145.118 |
| Interval indexes | −22 ≤ h ≤ 21, −9 ≤ k ≤ 10, −9 ≤ l ≤ 17 |
| Collected reflections | 7437 |
| Independent reflections | 2936 [Rint = 0.0195, Rsigma = 0.0191] |
| Data/restrictions/parameters | 2936/1/290 |
| Goodness of fit over F2 | 1.050 |
| Final R Indexes [I >= 2σ (I)] | R1 = 0.0339, wR2 = 0.0879 |
| Final R Indexes [all data] | R1 = 0.0342, wR2 = 0.0882 |
| Main difference of peak/orifice/e Å$^{-3}$ | 0.36/−0.18 |

Dissolution of the Crystalline NSF DSV:3,4-DHB

Figure 13:
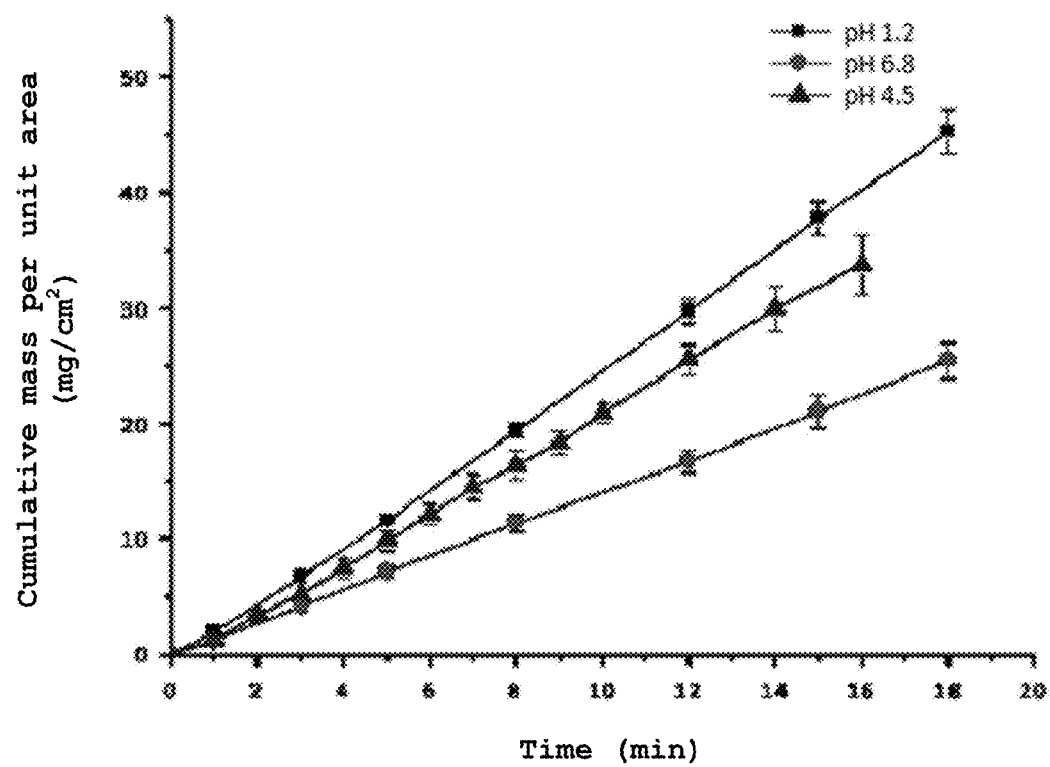
FIG. 13. Dissolution graph for the new crystalline solid phase of desvenlafaxine-3,4-dihydroxybenzoic acid at pH 1.2, 4.5 and 6.8.

Dissolution profiles were assessed for the crystalline NSF of DSV:3,4-DHB. The dissolution test was carried out at three pH values (1.2, 4.5 y 6.8) and the profiles are shown in FIG. 13. The rate constant values are grouped in Table 6.

TABLE 6

Intrinsic dissolution rate constants for the crystalline NSF DSV: 3,4-DHB evaluated at pH 1.2, 4.5 and 6.8

| | k (mg/cm2 · min) | S.D. | R2 |
|---|---|---|---|
| pH 1.2 | 2.48 | 0.042 | 0.9988 |
| pH 4.5 | 2.19 | 0.059 | 0.9988 |
| pH 6.8 | 1.43 | 0.046 | 0.9987 |

Figure 14:
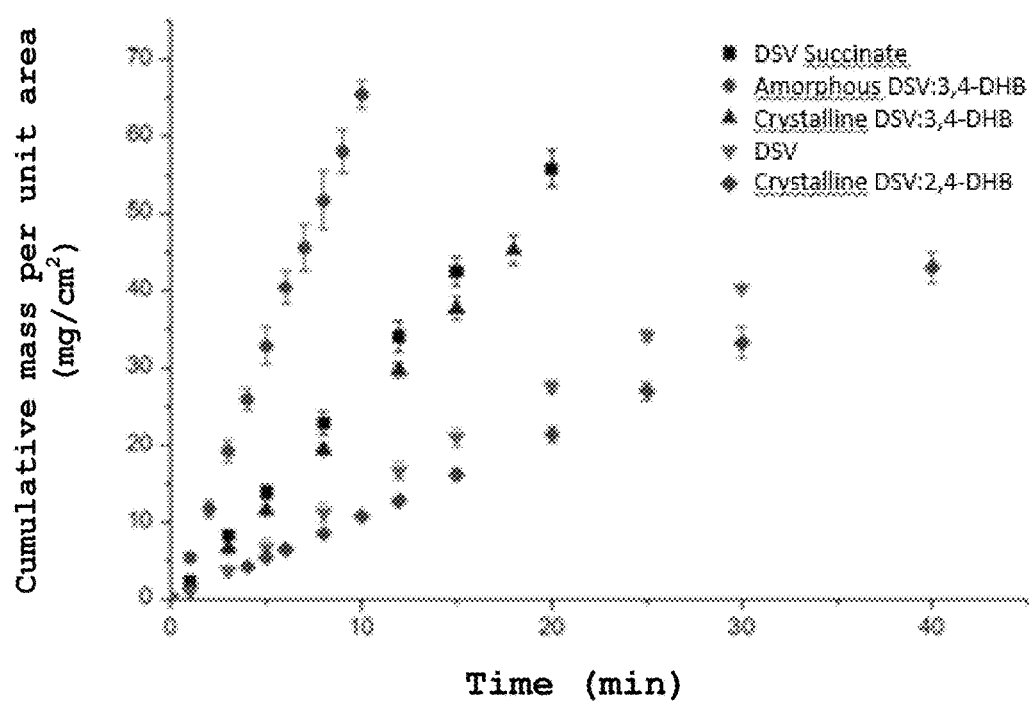
FIG. 14. Dissolution profile in HCl solution (pH 1.2, 37° C., 50 rpm, n=3, ±SD) of the new crystalline solid phase of desvenlafaxine-3,4-dihydroxybenzoic acid (crystalline DSV:3,4-DHB), and comparison with the new amorphous solid phase of desvenlafaxine-3,4-dihydroxybenzoic acid (amorphous DSV:3,4-DHB), the new crystalline solid phase of desvenlafaxine-2,4-dihydroxybenzoic acid (crystalline DSV:2,4-DHB), desvenlafaxine (DSV), and desvenlafaxine succinate (DSV succinate).
Figure 15:
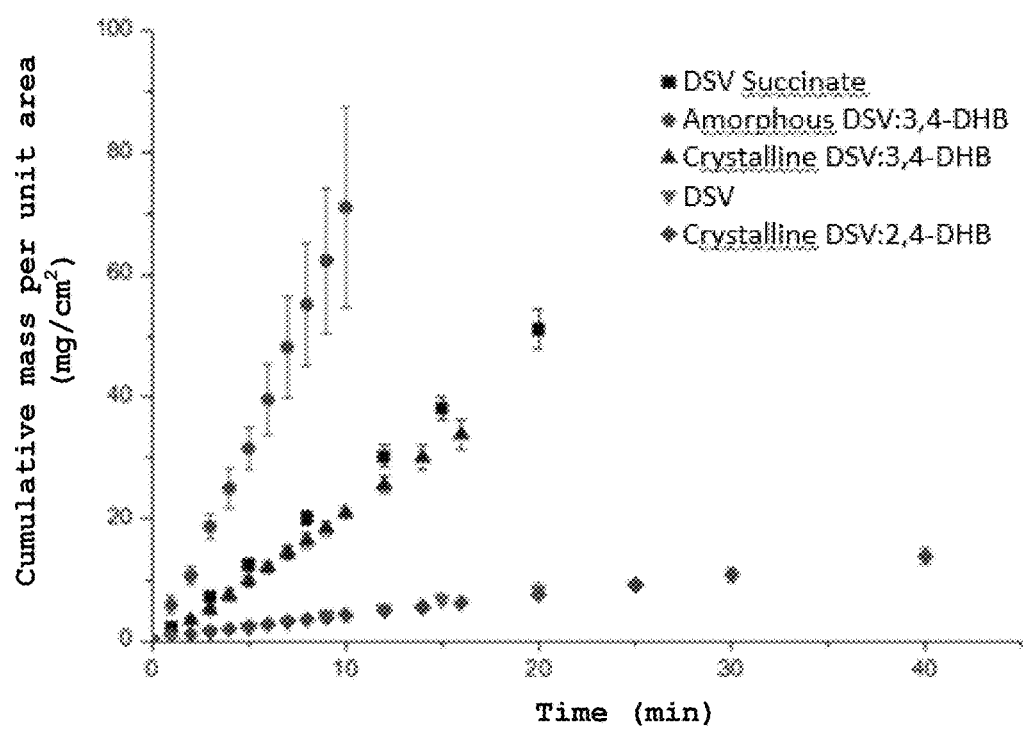
FIG. 15. Dissolution profile in acetate buffer (pH 4.5, 37° C., 50 rpm, n=3, ±SD) of the new crystalline solid phase of desvenlafaxine-3,4-dihidroxibenzoic acid (crystalline DSV:3,4-DHB), and comparison with the new amorphous solid phase of desvenlafaxine-3,4-dihydroxybenzoic acid (amorphous DSV:3,4-DHB), the new crystalline solid phase of desvenlafaxine-2,4-dihydroxybenzoic acid (crystalline DSV:2,4-DHB), desvenlafaxine (DSV), and desvenlafaxine succinate (DSV succinate).
Figure 16:
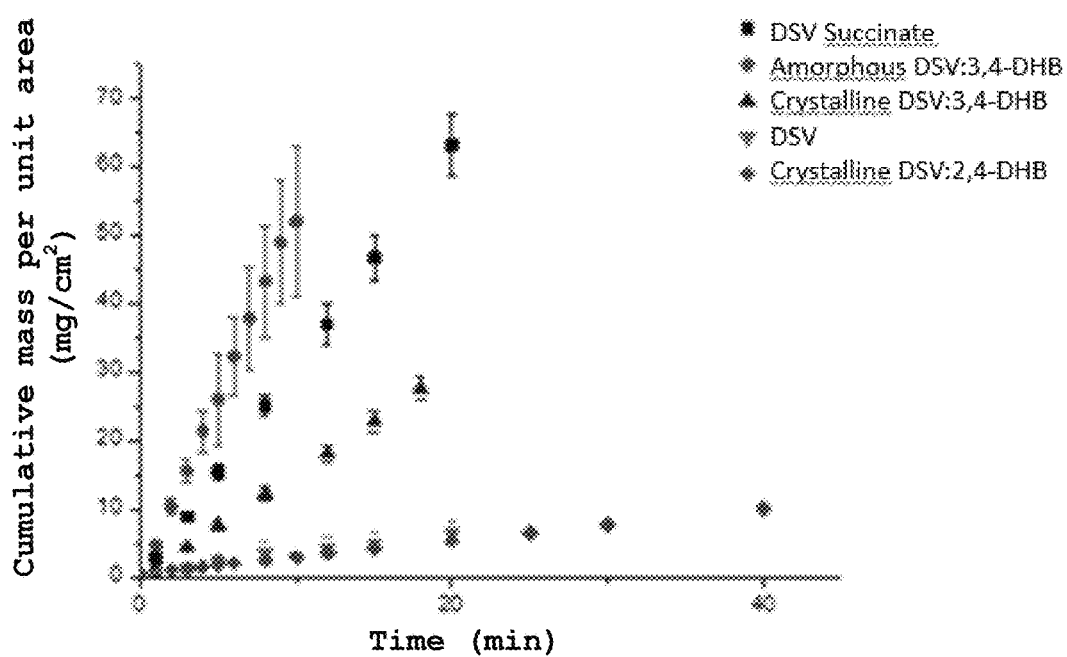
FIG. 16. Dissolution profile in phosphate buffer (pH 6.8, 37° C., 50 rpm, n=3, ±SD) of the new crystalline solid phase of desvenlafaxine-3,4-dihydroxybenzoic acid (crystalline DSV:3,4-DHB), and comparison with the new amorphous solid phase of desvenlafaxine-3,4-dihydroxybenzoic acid (amorphous DSV:3,4-DHB), the new crystalline solid phase of desvenlafaxine-2,4-dihydroxybenzoic acid (crystalline DSV:2,4-DHB), desvenlafaxine (DSV), and desvenlafaxine succinate (DSV succinate).

A comparative test was carried out for the dissolution profiles at pH 1.2, 4.5 and 6.8 for the new crystalline phase DSV:3,4-DHB with respect to the amorphous NSF with the same co-former, the crystalline NSF with 2,4-dihydroxybenzoic acid, as well as desvenlafaxine base and the commercial salt (desvenlafaxine succinate). These profiles are shown in FIGS. 14, 15 and 16. FIG. 14 shows the dissolution profiles in HCl solution (pH 1.2). FIG. 15 shows the dissolution profiles in acetate buffer (pH 4.5) and FIG. 16 shows the dissolution profiles in phosphate buffer (pH 6.8).

FIGS. 14 and 15 show the crystalline new phase of DSV:3,4-DHB at pH 1.2 and 4.5 presenting an intrinsic dissolution rate similar to that of the commercial form, which is found as the succinate salt. The solid phase that presents the higher dissolution rate is the amorphous NSF of DSV:3,4-DHB.

At the assessed pH (1.2, 4.5 y 6.8) the crystalline NSF with 2,4-dihydroxybenzoic acid has a lower dissolution rate than the commercial salt (succinate) and any of the other shown phases.

The intrinsic dissolution rate constant values for the five samples, are shown in Table 7.

TABLE 7

| | Dissolution rate constants (k) | | | | | |
|---|---|---|---|---|---|---|
| | pH 1.2 | | pH 4.5 | | pH 6.8 | |
| | k (cum. mg/cm$^2$) | Quotient ($k_{NSF}/k_{DSV}$) | k (cum. mg/cm$^2$) | Quotient ($k_{NSF}/k_{DSV}$) | k (cum. mg/cm$^2$) | Quotient ($k_{NSF}/k_{DSV}$) |
| DSV | 1.35 | — | 0.37 | — | 0.32 | — |
| DSV-Succinate | 2.86 | 2.1 | 2.57 | 6.9 | 3.19 | 10.0 |
| Crystalline DSV:3,4-DHB | 2.47 | 1.8 | 2.19 | 5.9 | 1.54 | 4.8 |
| Amorphous DSV:3,4-DHB | 6.69 | 5.0 | 6.81 | 18.4 | 5.45 | 17.0 |
| Crystalline DSV:2,4-DHB | 1.07 | 0.79 | 0.35 | 0.94 | 0.23 | 0.71 |

Optionally, the new solid forms obtained through the mentioned processes can be subjected to an additional purification process for drastically decreasing or eliminating residual solvents, which consist of:

Mixing the NSF and an alcoholic solvent in a container

Heating until dissolution and maintaining at a temperature between 70° C. and 90° C. for about 10-80 minutes Concentrating until solvent volume reaches one fourth of its original value and cooling down to 10° C.-15° C.

Filtering, washing with an alcoholic solvent and drying.

The alcoholic solvent can be selected from ethanol, hexane, isopropyl alcohol and methanol.

Table 8 shows the results of the two samples of NSF with 3,4-DHB acid, subjected to a purification process.

TABLE 8

Assessment results of the two purified samples of NSF with 3,4-DHB acid

| | NSF Sample 1 | NSF Sample 2 | Specification |
|---|---|---|---|
| DSV assessment | 99% | 99% | 90% minimum |
| 3,4-DHB assessment | 99% | 98% | 90% minimum |
| Residual solvent Acetone | 0 ppm | 0 ppm | 5,000 ppm maximum |
| Residual solvent Hexane | 0 ppm | 0 ppm | 390 ppm maximum |
| Residual solvent Ethanol | 1965 ppm | 3885 ppm | 5,000 ppm maximum |

With the obtained results, we can confirm that the purification method proposed in the present invention is innovative to obtain a product that complies with the specifications.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An amorphous solid compound formed by desvenlafaxine and a co-former X, wherein X is selected from the group consisting of 3-hydroxybenzoic acid, 3,4-dihydroxybenzoic acid, and 3,4,5-trihydroxybenzoic acid; or any solvate or hydrate of the amorphous solid compound.

2. A crystalline solid compound formed by desvenlafaxine and a co-former X, wherein X is selected from the group consisting of 2,4-dihydroxybenzoic acid and 3,4-dihydroxybenzoic acid, or any solvate or hydrate of the crystalline solid compound.

3. The crystalline solid compound of claim 2, wherein the co-former X is 3,4-dihydroxybenzoic acid, and wherein the crystalline solid compound is characterized by a powder X-ray diffraction pattern as illustrated in FIG. 7 obtained using CuKα radiation.

4. A pharmaceutical composition containing the compound of claim 1 and one or more pharmaceutically acceptable excipients.

5. The crystalline solid compound of claim 2, wherein the co-former X is 2,4-dihydroxybenzoic acid, and wherein the crystalline solid compound is characterized by a powder X-ray diffraction pattern as illustrated in FIG. 10 obtained using CuKα radiation.

* * * * *